US009370498B2

(12) United States Patent
Dobak

(10) Patent No.: US 9,370,498 B2
(45) Date of Patent: *Jun. 21, 2016

(54) METHODS OF USING LIPOLYTIC FORMULATIONS FOR REGIONAL ADIPOSE TISSUE TREATMENT

(75) Inventor: John Daniel Dobak, La Jolla, CA (US)

(73) Assignee: NEOTHETICS, INC., San Diego, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 12/763,030

(22) Filed: Apr. 19, 2010

(65) Prior Publication Data

US 2011/0105446 A1 May 5, 2011

Related U.S. Application Data

(62) Division of application No. 11/457,436, filed on Jul. 13, 2006, now Pat. No. 7,829,554.

(60) Provisional application No. 60/699,155, filed on Jul. 14, 2005, provisional application No. 60/729,531, filed on Oct. 24, 2005, provisional application No. 60/732,981, filed on Nov. 3, 2005.

(51) Int. Cl.
| | | |
|---|---|---|
| *A01N 45/00* | (2006.01) |
| *A61K 31/56* | (2006.01) |
| *A01N 43/40* | (2006.01) |
| *A61K 31/445* | (2006.01) |
| *A01N 37/18* | (2006.01) |
| *A61K 31/16* | (2006.01) |
| *A01N 33/02* | (2006.01) |
| *A61K 31/135* | (2006.01) |
| *A61K 31/138* | (2006.01) |
| *A61K 9/00* | (2006.01) |
| *A61K 31/573* | (2006.01) |
| *A61K 47/10* | (2006.01) |
| *A61K 47/14* | (2006.01) |
| *A61K 47/34* | (2006.01) |
| *A61K 47/36* | (2006.01) |
| *A61K 31/167* | (2006.01) |
| *A61K 31/4535* | (2006.01) |
| *A61K 31/567* | (2006.01) |
| *A61K 31/58* | (2006.01) |
| *A61K 31/195* | (2006.01) |
| *A61K 9/50* | (2006.01) |

(52) U.S. Cl.
CPC ............ *A61K 31/138* (2013.01); *A61K 9/0014* (2013.01); *A61K 9/0019* (2013.01); *A61K 9/0021* (2013.01); *A61K 31/167* (2013.01); *A61K 31/195* (2013.01); *A61K 31/4535* (2013.01); *A61K 31/567* (2013.01); *A61K 31/573* (2013.01); *A61K 31/58* (2013.01); *A61K 47/10* (2013.01); *A61K 47/14* (2013.01); *A61K 47/34* (2013.01); *A61K 47/36* (2013.01); *A61K 9/5031* (2013.01)

(58) Field of Classification Search
CPC . A61K 31/138; A61K 31/167; A61K 31/195; A61K 31/4535; A61K 31/567; A61K 31/573; A61K 31/58; A61K 47/10; A61K 47/14; A61K 47/34; A61K 47/36; A61K 9/0014; A61K 9/0019; A61K 9/0021; A61K 9/5031
USPC .................................. 514/171, 479, 653, 324
See application file for complete search history.

(56) References Cited

U.S. PATENT DOCUMENTS

| | | | |
|---|---|---|---|
| 4,525,359 A | 6/1985 | Greenway et al. |
| 4,800,079 A | 1/1989 | Boyer |
| 4,826,879 A | 5/1989 | Yamamoto et al. |
| 5,126,147 A | 6/1992 | Silvestri et al. |
| 5,270,305 A | 12/1993 | Palmer |
| 5,314,916 A | 5/1994 | York et al. |
| 5,496,803 A | 3/1996 | Meier et al. |
| 5,658,549 A | 8/1997 | Akehurst et al. |
| 5,709,884 A * | 1/1998 | Trofast et al. ................. 424/489 |
| 5,855,913 A | 1/1999 | Hanes et al. |
| 5,919,827 A * | 7/1999 | Barberich et al. ............ 514/651 |
| 5,972,919 A | 10/1999 | Carling |
| 6,030,604 A | 2/2000 | Trofast |
| 6,066,675 A | 5/2000 | Wen et al. |
| 6,110,974 A | 8/2000 | Aberg et al. |

(Continued)

FOREIGN PATENT DOCUMENTS

| | | |
|---|---|---|
| CA | 2500065 | 5/2004 |
| CA | 2588168 | 6/2006 |

(Continued)

OTHER PUBLICATIONS

Beers et al., "The Merck Manual", 1999, Merck and Co., NJ, USA, pp. 706-707.
Bruns et al., "Regulation of lipolysis in isolated human adipose-tissue cells," Lancet 1(7441):797-798 (1966).
Goodman, "Permissive effects of hormones on lypolysis," Endocrinology 86(5):1064-1074 (1970).
Louis et al., "Role of β-Adrenergic Receptor Subtypes in Lipolysis," Cardiovascular Drugs and Therapy 14(6):565-577 (2000).
Yip et al., "Growth hormones and dexamethasone stimulate lipolysis and active adenylyl cyclase in rat adipocytes by selectrively shifting Gi alpha2 to lower density membrane fractions," Endocrinology 140(3):1219-1227 (1999.

(Continued)

Primary Examiner — Uma Ramachandran
(74) Attorney, Agent, or Firm — Wilson Sonsini Goodrich & Rosati

(57) ABSTRACT

Compositions, formulations, methods, and systems for treating regional fat deposits comprise contacting a targeted fat deposit with a composition comprising long acting beta-2 adrenergic receptor agonist and a compound that reduces desensitization of the target tissue to the long acting beta-2 adrenergic receptor agonist, for example, glucocorticosteroids and/or ketofien. Embodiments of the composition are administered, for example, by injection, and/or transdermally.

18 Claims, 1 Drawing Sheet

(56) References Cited

U.S. PATENT DOCUMENTS

| | | |
|---|---|---|
| 6,316,443 B1 | 11/2001 | Baldwin et al. |
| 6,384,259 B1 | 5/2002 | Stogniew et al. |
| 6,537,983 B1 | 3/2003 | Biggadike et al. |
| 6,643,212 B1 | 11/2003 | Jones, Jr. et al. |
| 6,656,508 B2 | 12/2003 | Goldenberg et al. |
| 6,688,311 B2 | 2/2004 | Hanin |
| 6,743,413 B1 | 6/2004 | Schultz et al. |
| 6,869,942 B2 | 3/2005 | Trofast et al. |
| 7,140,371 B2 | 11/2006 | Hanin et al. |
| 7,172,752 B2 | 2/2007 | Watanabe et al. |
| 7,234,469 B2 | 6/2007 | Hanin |
| 7,253,156 B2 | 8/2007 | Currie et al. |
| 7,267,813 B2 | 9/2007 | Watanabe et al. |
| 7,348,362 B2 | 3/2008 | Banerjee et al. |
| 7,354,913 B2 | 4/2008 | Trofast et al. |
| 7,638,508 B2 | 12/2009 | Biggadike et al. |
| 7,662,815 B2 | 2/2010 | McKinnell et al. |
| 7,666,912 B2 | 2/2010 | Grosskreutz et al. |
| 7,723,392 B2 | 5/2010 | Aberg et al. |
| 7,829,554 B2 | 11/2010 | Dobak |
| 8,101,593 B2 | 1/2012 | Hodge et al. |
| 8,367,649 B2 | 2/2013 | Hodge et al. |
| 8,404,750 B2 | 3/2013 | Dobak et al. |
| 8,420,625 B2 | 4/2013 | Dobak |
| 8,426,471 B1 | 4/2013 | Kalayoglu et al. |
| 8,569,376 B2 | 10/2013 | Kalayoglu et al. |
| 8,653,058 B2 | 2/2014 | Hodge et al. |
| 8,883,834 B2 | 11/2014 | Kalayoglu et al. |
| 2002/0032149 A1 | 3/2002 | Kensey |
| 2002/0042404 A1 | 4/2002 | Bauer et al. |
| 2003/0022856 A1 | 1/2003 | Richardson et al. |
| 2003/0022911 A1 | 1/2003 | Smith et al. |
| 2003/0077305 A1 | 4/2003 | McDonald et al. |
| 2003/0095925 A1 | 5/2003 | Dugger |
| 2003/0161207 A1 | 8/2003 | Jones, Jr. et al. |
| 2003/0236238 A1 | 12/2003 | Trofast et al. |
| 2004/0037875 A1 | 2/2004 | Metselaar et al. |
| 2004/0043032 A1 | 3/2004 | McKenzie et al. |
| 2004/0171597 A1 | 9/2004 | Biggadike et al. |
| 2004/0208833 A1 | 10/2004 | Hovey et al. |
| 2004/0208910 A1 | 10/2004 | Ashton et al. |
| 2004/0209850 A1 | 10/2004 | Babul |
| 2004/0235922 A1 | 11/2004 | Baile et al. |
| 2004/0247628 A1 | 12/2004 | Lintz et al. |
| 2005/0048127 A1 | 3/2005 | Brown et al. |
| 2005/0069591 A1 | 3/2005 | Bernstein et al. |
| 2005/0075900 A1 | 4/2005 | Arguimbau |
| 2005/0089555 A1 | 4/2005 | Boderke et al. |
| 2005/0113456 A1 | 5/2005 | Aberg |
| 2005/0141293 A1 | 6/2005 | Ha |
| 2005/0207989 A1 | 9/2005 | Trofast et al. |
| 2005/0222108 A1 | 10/2005 | Bhatarah et al. |
| 2005/0244339 A1 | 11/2005 | Jauernig et al. |
| 2005/0267080 A1 | 12/2005 | Kolodney et al. |
| 2006/0051299 A1 | 3/2006 | Chaudry |
| 2006/0188579 A1 | 8/2006 | Rogueda |
| 2006/0189587 A9 | 8/2006 | Bauer et al. |
| 2007/0014843 A1 | 1/2007 | Dobak |
| 2007/0134158 A1 | 6/2007 | Hanin et al. |
| 2007/0140969 A1 | 6/2007 | Hanin et al. |
| 2007/0178051 A1 | 8/2007 | Pruitt |
| 2007/0178166 A1 | 8/2007 | Bernstein et al. |
| 2008/0097219 A1 | 4/2008 | Reser et al. |
| 2008/0157409 A1 | 7/2008 | Reens |
| 2008/0249017 A1 | 10/2008 | Loughrey et al. |
| 2008/0270175 A1 | 10/2008 | Rodriguez et al. |
| 2008/0300229 A1 | 12/2008 | Wilcox et al. |
| 2009/0123550 A1 | 5/2009 | Phillips |
| 2009/0275545 A1 | 11/2009 | Boderke et al. |
| 2010/0093693 A1 | 4/2010 | Shen et al. |
| 2010/0119609 A1 | 5/2010 | Dobak |
| 2010/0137267 A1 | 6/2010 | Dobak |
| 2010/0215710 A1 | 8/2010 | Isseroff et al. |
| 2010/0234466 A1 | 9/2010 | Grosskreutz et al. |
| 2011/0130373 A1 | 6/2011 | Dobak et al. |
| 2011/0166202 A1 | 7/2011 | Banerjee |
| 2011/0224176 A1 | 9/2011 | Dobak et al. |
| 2011/0230964 A1 | 9/2011 | Yacoub et al. |
| 2012/0015918 A1 | 1/2012 | Dobak |
| 2012/0046256 A1 | 2/2012 | Dobak |
| 2012/0046257 A1 | 2/2012 | Dobak et al. |
| 2012/0169732 A1 | 7/2012 | Mordaunt et al. |
| 2012/0178819 A1 | 7/2012 | Dobak |
| 2012/0237492 A1 | 9/2012 | Walker |
| 2012/0329765 A1 | 12/2012 | Boderke et al. |
| 2013/0060123 A1 | 3/2013 | Mordaunt et al. |
| 2013/0190282 A1 | 7/2013 | Hodge et al. |
| 2014/0045933 A1 | 2/2014 | Kalayoglu |
| 2014/0074237 A1 | 3/2014 | Yacoub et al. |
| 2014/0094662 A1 | 4/2014 | Van et al. |
| 2014/0142075 A1 | 5/2014 | Kalayoglu et al. |
| 2014/0148429 A1 | 5/2014 | Hodge et al. |
| 2014/0163098 A1 | 6/2014 | Grosskreutz et al. |
| 2014/0322305 A1 | 10/2014 | Dobak et al. |

FOREIGN PATENT DOCUMENTS

| | | |
|---|---|---|
| CA | 2615173 | 1/2007 |
| CA | 2628178 | 5/2007 |
| CA | 2631493 | 6/2007 |
| CA | 2640444 | 8/2007 |
| CA | 2666564 | 6/2008 |
| CA | 2827643 A1 | 8/2012 |
| CN | 1640390 | 7/2005 |
| CN | 1706501 | 12/2005 |
| EP | 0120165 | 7/1990 |
| EP | 1153614 | 11/2001 |
| EP | 1482986 B1 | 9/2006 |
| EP | 1867334 | 12/2007 |
| GB | 1471326 | 4/1977 |
| GB | 2443287 | 4/2008 |
| GB | 2453188 | 4/2009 |
| GB | 2470818 | 12/2010 |
| GB | 2477030 | 7/2011 |
| JP | 59-155313 | 9/1984 |
| JP | 61-31043 | 2/1986 |
| JP | S61246129 A | 11/1986 |
| JP | 11106334 | 4/1999 |
| JP | H11507936 A | 7/1999 |
| JP | 2004-513340 | 4/2004 |
| JP | 2005-508220 | 3/2005 |
| KR | 2008-0067705 | 7/2008 |
| KR | 2009-0112590 | 10/2009 |
| WO | WO-9812228 A1 | 3/1998 |
| WO | WO-98-41232 | 9/1998 |
| WO | WO 98/48810 | 11/1998 |
| WO | WO 01/19373 | 3/2001 |
| WO | WO 01/28535 | 4/2001 |
| WO | WO 03/033000 | 4/2003 |
| WO | WO-03077954 A1 | 9/2003 |
| WO | 2004-028545 | 4/2004 |
| WO | WO 2004/028545 | 4/2004 |
| WO | WO-2004030659 A1 | 4/2004 |
| WO | WO 2004/091574 | 10/2004 |
| WO | WO 2004/103057 | 12/2004 |
| WO | WO 2004/103379 | 12/2004 |
| WO | WO 2005/007145 | 1/2005 |
| WO | WO 2005/072745 | 8/2005 |
| WO | WO-2006086001 A2 | 8/2006 |
| WO | WO 2006/122165 | 11/2006 |
| WO | WO 2007/011743 | 1/2007 |
| WO | WO-2007-117661 A2 | 10/2007 |
| WO | WO-2007111806 A2 | 10/2007 |
| WO | WO-2008-048770 | 4/2008 |
| WO | WO-2008-066775 | 6/2008 |
| WO | WO-2008-067060 | 6/2008 |
| WO | WO-2008-157409 A1 | 12/2008 |
| WO | WO-2009-000473 | 12/2008 |
| WO | WO-2010045579 A2 | 4/2010 |
| WO | WO-2010045581 A1 | 4/2010 |
| WO | WO-2010-138770 A2 | 12/2010 |
| WO | WO-2010-138770 A3 | 12/2010 |
| WO | WO-2011-088413 | 7/2011 |
| WO | WO-2012099942 A2 | 7/2012 |

(56) References Cited

FOREIGN PATENT DOCUMENTS

| WO | WO-2012112940 A1 | 8/2012 |
|----|------------------|--------|
| WO | WO-2013096429 A2 | 6/2013 |
| WO | WO-2014055895 A1 | 4/2014 |
| WO | WO-2014081941 A1 | 5/2014 |

OTHER PUBLICATIONS

EP07843370 Search Report mailed Mar. 11, 2010.
EP06787329.9 Office Action mailed Jan. 31, 2011.
Office action mailed Jan. 6, 2010 in connection with U.S. Appl. No. 11/457,436.
Office action mailed Aug. 24, 2009 in connection with U.S. Appl. No. 11/457,436.
GB 0718905.3 combined search and examination report dated Jan. 28, 2008.
GB 0718905.3 search report dated Nov. 27, 2008, claims 31-33.
GB 0718905.3 search report dated Nov. 27, 2008, claims 34-37 and 44.
GB 0718905.3 examination report dated Nov. 27, 2008.
AU2006270165 examiner's first report dated Dec. 24, 2009.
GB 0804401.8 search report dated Apr. 15, 2009.
PCT/US2007/079740 search report mailed Jan. 30, 2008.
EP 07871172 supplementary European search report dated Mar. 1, 2010.
PCT/US2007/081568 search report mailed Jun. 17, 2008.
Adcock, "Molecular interactions between glucocorticoids and long-acting $\beta_2$-agonists," J Allergy Clin Immunol 110(6 Suppl):S261-8 (2002).
Arner et al., "Human fat cell lipolysis: biochemistry, regulation and clinical role," Best Practice & Research Clinical Endocrinology & Metabolism 19:471-482 (2005).
Brodde et al., "Terbutaline-induced desensitization of human lymphocyte beta 2-adrenoceptors. Accelerated restoration of beta-adrenoceptor responsiveness by prednisone and ketotifen," J Clin Invest 76(3):1096-101 (1985).
Bronnegard et al., "Effect of glucocorticosteroid treatment on glucocorticoid receptor expression in human adipocytes," J Clin Endocrinol Metab 80(12):3608-12 (1995).
Bujalska et al., "Characterisation of 11$\beta$-hydroxysteroid dehydrogenase 1 in human orbital adipose tissue: a comparison with subcutaneous and omental fat," J Endocrinol 192(2):279-88 (2007).
Caruso et al., "Topical fat reduction from the waist," Diabetes Obesity Metabolism 9:300-303 (2007).
Chung, "The complementary role of glucocorticosteroids and long-acting beta-adrenergic agonists," Allergy 53(42 Suppl):7-13 (1998).
De Mazancourt et al., "Correction by dexamethasone treatment of the altered lipolytic cascade induced by adrenalectomy in rat adipocytes," Horm Metab Res 22(1):22-4 (1990).
Farias-Silva et al., "Glucocorticoid receptor and Beta-adrenoceptor expression in epididymal adipose tissue from stressed rats," Ann NY Acad Sci 1018:328-32 (2004).
Fries, "Thyroid dysfunction: managing the ocular complications of Graves' disease," Geriatrics 47(2):58-60, 63-4, 70 (1992).
Fuller et al., "Fluticasone propionate—an update on preclinical and clinical experience," Respir Med 89 Suppl A:3-18 (1995).
Gibaud et al., "Poly($\epsilon$-caprolactone) and Eudragit microparticles containing fludrocortisone acetate," Int J Pharm 28;269(2):491-508 (2004).
Gittoes and Franklyn, "Hyperthyroidism. Current treatment guidelines," Drugs 55(4):543-53 (1998).
Hadcock and Malbon, "Regulation of $\beta$-adrenergic receptors by "permissive" hormones: glucocorticoids increase steady-state levels of receptor mRNA," Proc Natl Acad Sci U S A 85(22):8415-9 (1988).
Johnson, "The $\beta$-Adrenoceptor," Am J Resp Crit Care Med 158:146-153 (1998).
Johnson, "$\beta$-2-adrenoceptors: mechanisms of action of $\beta$-2-agonists," Ped Resp Rev 2:57-62 (2001).
Kendall-Taylor et al., "Intravenous methylprednisolone in the treatment of Graves' ophthalmopathy," BMJ 297(6663):1574-8 (1988).
Lacasa et al., "Permissive action of glucocorticoids on catecholamine-induced lipolysis: direct "in vitro" effects on the fat cell beta-adrenoreceptor-coupled-adenylate cyclase system," Biochem Biophys Res Commun 153(2):489-97 (1988).
Langley et al., "Perioperative management of the thyrotoxic patient," Endocrinol Metab Clin North Am 32(2):519-34 (2003).
Mak et al., "Protective effects of a glucocorticoid on downregulation of pulmonary beta 2-adrenergic receptors in vivo," J Clin Invest 96(1):99-106 (1995).
Marcocci et al., "Orbital cobalt irradiation combined with retrobulbar or systemic corticosteroids for Graves' ophthalmopathy: a comparative study," Clin Endocrinol (Oxf) 27(1):33-42 (1987).
Mirkin, "Albuterol for weight control," www.DrMirkin.com (2009).
Page et al., "$\beta$-Adrenergic receptor agonists increase apoptosis of adipose tissue in mice," Domest Anim Endocrinol 26(1):23-31 (2004).
Pedersen et al., "Anti-glucocorticoid effects of progesterone in vivo on rat adipose tissue metabolism," Steroids 68:543-550 (2003).
Reynisdottir et al., "Effect of glucocorticosteroid treatment on beta-adrenoceptor subtype function in adipocytes from patients with asthma," Clin Sci 85(2):237-44 (1993).
Risse-Sundermann, "The treatment of alopecia areata by intradermal injections of microcrystallized prednisone trimethylacetate," Dtsch med Wochenschr 85(15):584-586 (1960).
Seco et al., "Acute and chronic treatment with glucocorticosteroids, modifying the beta 2-adrenergic response of the guinea pig trachea," Lung 173(5):321-8 (1995).
West, "Solid state chemistry and its applications," Wiley, New York, pp. 358-365 (1988).
Wiersinga and Prummel, "Graves' ophthalmopathy: a rational approach to treatment," Trends Endocrinol Metab 13(7):280-7 (2002).
Dobak, "Formulations for Treatment of Adipose Tissue, Cutaneous Tissue and Disorders, and Muscular Tissue," U.S. Appl. No. 12/445,571, filed Jan. 22, 2010.
Dobak, "Methods, Compositions, and Formulations for the Treatment of Thyroid Eye Disease," U.S. Appl. No. 12/445,570, filed Jan. 12, 2010.
Gronneberg, "Effects of local treatment with salmeterol and terbutaline on anti-IgE-induced wheal, flare, and late induration in human skin," Allergy 51(10):685-692 (1996).
Mersmann, "Beta-Adrenergic receptor modulation of adipocyte metabolism and growth," J Animal Science 80:E24-E29 (2002).
PCT/US10/36484 Search Report and Written Opinion mailed Feb. 21, 2011.
EP 06787329.9 extended European search report dated Mar. 12, 2010.
Cuirong, Study on the Effect of Hyaluronidase on Orbital Fibroblast, Chinese M.M. thesis, 2006, p. 2.
GB1100628.5 Search and Examination Report mailed Apr. 11, 2011.
Hiromatsu, *Basedow's disease*, Japanese Publication New Regional Sales, No. 1, Syndromes, May 26, 2006, Second Ed., pp. 307-310.
Laurent and Scopes, *Hyaluronidase in the treatment of exophthalmic opthalmoplegia*, Sep. 10, 1955, 269 Edition No. 6889, pp. 537-538.
Nakai et al., "Hypothyroid Grave's Disease concurring with TSAb clarity high value shown in Hashimoto's disease," Industrial Medical University Magazine 25(3):333-339 (2003).
Murano, *Selection of Treatment Methods for Basedow's Disease*, Modern Physician, Jul. 2003, 23 Ed. 7, pp. 1103-1111.
Yokoyama, Basedow's Disease Diagnosis and Treatment, 2005, 93 Ed. No. 7, pp. 1077-1081.
GB 1008885.4 combined search and examination report dated Sep. 29, 2010.
Caruso et al., "An evaluation of mesotherapy solutions for inducing lipolysis and treating cellulite," J Plast Reconstr Aesthet Surg. 61(11):1321-4, 2008. Epub Oct. 22, 2007.
Arner, et al. "Adreneroic Regulation of Lipolysis In Situ at Rest and during Exercise," J. Clin. Invest., vol. 85, pp. 893-898 (1990).
Arner, et al,, "In Vivo Interactions between Beta-1 and Beta-2 Adrenoceptors Regulate Catecholamine Tachyphylaxia in Human Adipose Tissue," Journ. Pharm. Exper. Therap., vol. 259, No. 1, pp. 317-322 (1991).

(56) References Cited

OTHER PUBLICATIONS

Arner, et al., "Adrenergic Receptor Function in Fat Cells1-3," Am. J. Clin. Nutr. 55:228S-36S (1992).
Barbe, et al., "In situ assessment of the role of the β1-,β2- and β3 adrenoceptors in the control of lipolysis and nutritive blood flow in human subcutaneous adipose tissue," British Journ. Pharma. (1996) 11 (7 pgs.).
Barbe, et al., "In Vivo Increase in β-Adrenergic Lipolytic Response in Subcutaneous Adipose Tissue of Obese Subject Submitted to a Hypocaloric Diet," Journ. Clin. Endocrin. and Metab., vol. 82, No. 1, pp. 63-69 (1997).
Barnes, "Scientific rationale for inhaled combination therapy with long-acttng β2-agonists and corticosteroids," Eur Respir Journ. 19:182-191 (2002).
Bartalena et al., "Management of Graves' Ophthalmopathy: Reality and Perspectives," Endocrine Reviews 21(2): 168-199 (2000).
Bartley, "The Epidemiologic Characteristics and Clinical Course of Ophthalmopathy Associated with Autoirnmune Thyroid Disease in Olmstead County, Minnesota," Th. Am. Ophth. Soc, vol. XCII, (112 pgs.)(1994).
Bartley et al, "Clinical Features of Graves' Ophthalmopathy in an Incidence Cohort," Amer. Journ. Ophthalmology, 121:284-290 (1996).
Basadonna et al., "Plantar Fat Pad Atrophy After Corticosteroid Injection for an Interdigital Neuroma," Amer. Journ. Phys. Med. Rehabil. 1999; 78:283-285.
Benovic et al.. "Regulation of adenylyl cyclase-coupled β-adrenergic receptors." Ann Rev Cell Biol 1988; 4: 405-428.
Benzon et al., "Comparison of the Particle Sizes of Different Steroids and the Effect of Dilution," Anesthesiology, 106:331-8 (2007).
Bordaberry et al., "Repeated Peribulbar Injections of Triamcinolone Acetonide: a Successful and Safe Treatment for Moderate to Severe Graves' Ophthalmopathy," ACTA Ophthalmologica 2009; 87:58-64.
Bousquet-Melou, "beta-Adrenergic control of lipolysis in primate white fat cells: a comparative study with nonprimate mammals," Am J Physiol Regulatory Integrative Comp Physiol 267:115-123 (1994).
Carpene et al., "Adrenergic lipolysis in guinea pig is not a beta 3-adrenergic response: comparison with human adipocytes," Am J Physioi Regulatory Integrative Comp Physiol 266:905-913 (1994).
Caruso et al. "An evaluation of mesotherapy solutions for inducing . . . " J Plast Reconstr Aesthet Surg. 61(11):1321-4, Epub2007 (2008).
Clauser et al., "Rationale of Treatment in Graves Ophthalmopathy," Plastic and Reconstructive Surgery, pp. 1880-1894 Dec. 2001.
Collins et al., "Learning new tricks from old dogs: β-adrenergic receptors teach new lessons on firing up adipose tissue metabolism," Molecular Endocrinology First published Jul. 8, 2004 as doi:10.1210/me.2004-0193 (22 pgs.) (2004).
De Ponte et al., "New Approach to the Surgical Treatment of Severe Exophthalmos in Graves Disease," J. Craniofacial Surgery, vol. 9, No. 4, pp. 394-399 (1998).
Farias-Silva et al., "Stress-induces alteration in the lipolytic response to β-adrenoceptor agonists in rat white adipocytes," Journal of Lipid Research, vol. 40, 1719-1727 (1999).
Flechtner-Mors et al., "In Vivo α1-Adrenergic Lipolytic Activity in Subcutaneous Adipose Tissue of Obese Subjects," Journ. of Pharm. and Exper. Therap., vol. 301, No. 1, pp. 229-233 (2002).
Galitzky et al., "Coexistence of β1-, β2-, and β3-adrenoceptors in dog fat cells and their differential activation by catecholamines," The Amer. Physiol. Society pp. E403-E412 (1993).
Galitzky et al., "Differential activation of β1-, β2-, and β3-adrenoceptors by catecholamines in white and brown adipocytes," Fundam. Clin. Pliarinacol 9, 324-331 (1995).
Germack et al., "β-Adrenoceptor subtype expression and function in rat white adipocytes," British Journ. Pharma. 120, 201-210 (1997).
Gettys et al., "Age-Dependent Changes in β-Adrenergic Receptor Subtypes and Adenyly1 Cyclase Activation in Adipocytes from Fischer 344 Rats," Endocrinology, vol. 136, No. 5, pp. 2022-2032 (1995).
Giudicelli et al., Eur J Biochem 99(3):457-62 (1979).

Greenway et al., "Topical Fat Reduction," Obesity Research, vol. 3 Suppl. 561S-568S (1995).
Hall, et al. "Intravenous methylpredinisolone in the treatment of Graves; ophthalmopathy" BMJ 297(6663) 1574-1578 (1988).
Heine et al., "Increased adipose tissue in male and female estrogen receptor-α knockout mice,"PNAS, vol. 97, No. 23 12729-72734 (2000).
Hickey et al., Biomaterials 23:1649-1656, 2002.
January et al., "Salmeterol-induced desensitization, internalization and phosphorylation of the human β2-adrenoceptor." British Journal of Pharmacology 123:701-711 (1998).
Jockers et al., "Desensitization of the β-Adrenergic Response in Human Brown Adipocytes," Endocrinology, vol. 139, No. 6, pp. 2676-2684 (1998).
Johnson, "Interactions between Corticosteroids and β2-Agonists in Asthma and Chronic Obstructive Pulmonary Disease," Proc Am Thorn Soc, vol. 1, pp. 200-206 (2004).
Johnson et al. "The pharmacology of salmeterol." Life Sci 1993; 52: 2131-2143.
Kazim et al., "Reversal of dysthyroid optic neuropathy following orbital fat decompression," Br. J. Ophthalmol. 84:600-605 (2000).
Kolata "Calorie-burning fat? Studies say you have it" The New York Times, (Apr. 8, 2009).
Kumar et al., "Evidence for Enhanced Adipogenesis in the Orbits of Patients with Graves' Ophthalmopathy," Journ. Clin. Endocrin. & Metab. 89(2):930-935 (2004).
Lafontan. "Fat Cells: Afferent and efferent messages define new approaches to treat obesity." Ann Rev Pharmacol Toxicol 45: 119-146, (2005).
Lafontan and Berlan "Fat cell adrenergic receptors and the control of white and brown fat cell function" J Lipid Res 34:1057-1091 (1993).
Lai et al., "Dexamethasome Regulates the β-Adrenergic Receptor Subtype Expressed by 3T3-L1 Preadipocytes and Adipocytes," Journ. Biol. Chem. vol. 257, No. 12, pp. 6691-6696(1982).
Lonnqvist et al., "Lipolytic Catecholamine Resistance Due to Decreased β2-Adrenoceptor Expression in Fat Cells," J. Clint. Invest., vol. 90, pp. 2175-2186 (1992).
Mattson "Does brown fat protect against diseases of aging?" Ageing Res Rev 9(1):69-76 (2010).
Mauriege et al., "Human fat cell beta-adrenergic receptors: beta-agonist-dependent cell membranes with highly selective beta1-antagonists," Journ. Lipid Research, vol. 29, pp. 587-601 (1988).
Mori et al.. "Rapid desensitization of lipolysis in the visceral and subcutaneous adipocytes of rats." Lipids 2007; 42(4): 307-314.
Murano, "Selection of Treatment Methods for Basedow's disease" Modern Physician 23 Ed 7, pp. 1103-1111 (2003).
Ng et al, "Combined orbital irradiation and systemic steroids compared with systemic steroids alone in the management of moderate-to-severe Graves' ophthalmopathy: a preliminary study," Hong Kong Med. J., vol. 11, No. 5, pp. 322-330 (2005).
Ohkawara et al., "Glucorticoid-Induced Alteration of Beta-Adrenergic Adenylate Cyclase Response of Epidermis," Arch Dermatol Res 277:88-92 (1985).
Ohtsuka et al., "Effect of Steroid Pulse Therapy With and Without Orbital Radiotherapy on Graves' Ophthalmopathy," Am J Ophthalinol 135:285-290 (2003).
Papadopoulos et al., "The Clinical Picture: Soft Tissue Atrophy After Corticosteroid Injection," Cleveland Clinic Journ. Med., 2009; vol. 76 (6)373-374.
Sharma et al., "β-Adrenergic Receptor Blockers and Weight Gain A Systemic Analysis," Hypertension 37:250-254 (2001).
Taouis et al., "Characterization of Dog Fat Cell Adrenoceptors: Variations in Alpha-2 and Beta Adrenergic Receptors Distribution According to the Extent of the Fat Deposits and the Anatomical Location," Journ. Pharma. and Exper. Therap., vol. 242, No. 3. pp. 1041-1049 (1987).
PCT/US10/36484 IPRP mailed Nov. 29, 2011 with Written Opinion.
EP06787329.9 Extended European search rpt dated Mar. 12, 2010.
EP 11180982 Search Report mailed Nov. 21, 2011.
PCT/US2011/021424 International Search Report mailed Sep. 21, 2011.
IL 198184 Exam Report mailed Dec. 4, 2011.
GB 1100628.5 Examination Report mailed Feb. 6, 2012.

(56) References Cited

OTHER PUBLICATIONS

GB 1008885.4 Examination Report mailed Nov. 18, 2011.
MX 200800570 Office Action mailed Nov. 18, 2011.
U.S. Appl. No. 12/760,258, filed Apr. 14, 2010, Unpublished.
U.S. Appl. No. 13/284,741, filed Oct. 28, 2011, Unpublished.
U.S. Appl. No. 13/303,045, filed Nov. 22, 2011, Unpublished.
U.S. Appl. No. 13/303,046, filed Nov. 22, 2011, Unpublished.
FDA 2002, pp. 1-2 (Update on Illegal Compounding of Clenbuterol Veterinary Drug Products).
Mamani-Matsuda et al., Long-acting beta2-adrenergic formoterol and salmeterol induce the apoptosis of B-Chronic lymphocytic leukemia cells, Br J. Haematol. Jan. 2004;124(2), printed from http://www.ncbi.nlm.nih.gov/pubmed/14687023, Abstract only, 2 pages.
Mcrea et al., "Salmeterol, a long-acting beta 2-adrenoceptor agonist mediating cyclic AMP accumulation in a neuronal cell line," Br. J. Pharmacol. Oct. 1993;110(2), printed from http://www.ncbi.nlm.nih.gov/pubmed/7902176, Abstract only, 2 pages.
Sato et al., "Prediction for effectiveness of steroid pulse therapy in the orbits of patients with Graves' ophthalmopathy," Nihon Naibunpi Gakkai Zasshi. Mar. 20, 1992;68(3), printed from http://www.ncbi.nlm.nih.gov/pubmed/1582520, Abstract only, 2 pages.
AU 2010253864 First Examiner's Report dated Jun. 15, 2012.
GB 1207749 Exam Report dated May 15, 2012.
GB 1008885.4 Exam Report dated Jul. 31, 2012.
KR 10-2009-70099772 Office Action dated Apr. 25, 2012 (English translation).
PCT/US2011/061972 Search report dated Jun. 15, 2012.
PCT/US2011/021424 International Preliminary Report on Patentability and Written Opinion dated Jul. 17, 2012.
PCT/US06/027405 Search rpt mailed Aug. 28, 2007.
U.S. Appl. No. 12/445,570 Office Action dated May 22, 2012.
U.S. Appl. No. 12/788,190 Office Action dated Jul. 16, 2012.
U.S. Appl. No. 13/284,741 Office Action dated May 17, 2012.
U.S. Appl. No. 13/007,518 Office Action dated Sep. 12, 2012.
Dobak, Formulations and Methods for Activating Brown Adipose Tissue, U.S. Appl. No. 12/760,258, filed Apr. 14, 2010, Unpublished.
Dobak, "Formulations for Treatment of Adipose Tissue, Cutaneous Tissue and Disorders, and Muscular Tissue." U.S. Appl. No. 12/445,571, filed Jan. 22, 2010, Unpublished.
Dobak, "Methods. Compositions, and Formulations for the Treatment of Thyroid Eye Disease." U.S. Appl. No. 12/445,870, filed Jan. 12, 2010, Unpublished.
Shishiba, "Selection of Treatment Methods for Basedow's disease," Modern Physician 23, Ed. 7, pp. 1103-1111 (2003).
Boulet et al., "Influence of obesity on response to fluticasone with or without salmeterol in moderate asthma," Respiratory Medicine (2007) 101, 2240-2247.
CN 200680031397.4 Office Action dated Feb. 14, 2012.
CN 200780046741.1 Office Action dates Feb. 22, 2012.
EP11180982.8 Exam Report dated Mar. 14, 2012.
GB 1008885.4 Exam Report dated Apr. 4, 2012.
GB 1100628.5 Exam Report dated Feb. 6, 2012.
IL 198183 translation of Office Action dated Dec. 4, 2011.
U.S. Appl. No. 13/204,423 Office Action dated May 1, 2012.
U.S. Appl. No. 12/760,258 Office Action dated Apr. 2, 2012.
Ball et al. (1991) Salmeterol, a novel, long-acting beta 2-adrenoceptor agonist: characterization of pharmacological activity in vitro and in vivo. Br. J. Pharmacol. 104, 665-671.
CA 2,761,744 Examination Report dated Oct. 9, 2013.
Djurhuus et al. (2002). Effects of cortisol on lipolysis and regional interstitial glycerol levels in humans. American Journal of Physiology-Endocrinology and Metabolism 283, E172-E177.
EP1921919 B1 Opposition to a European patent dated Jun. 15, 2012.
GB 1207749.1 Exam Report issued Sep. 25, 2013.
Harrison (2004). The Medical Post, issue of Feb. 24, 2004, p. 5: "Love handles can be shrunk without surgery".
Harrison (2004). Excerpt from www.macleans.ca online forum, article dated Feb. 25, 2004: "Love handles can be shrunk without surgery".
Jensen (1997). Lipolysis: contribution from regional fat. Annu. Rev. Nut. 17, 127-139.
JP Application 2012-095792 Office Action dated Sep. 10, 2013 (English translation only).
JP 2011083171 Office Action dated Aug. 30, 2013 (including English Translation).
Kiri et al. Inhaled corticosteroids are more effective in COPD patients when used with LABA than with SABA. Respir Med. Sep. 2005;99(9):1115-1124.
Lamberts et al. (1975). The mechanism of the potentiating effect of glucocorticoids on catecholamine-induced lipolysis. Metabolism 24(6), 681-689.
Linden et al. (1996). Pharmacological basis for duration of effect: formoterol and salmeterol versus short-acting beta 2-adrenoceptor agonists. Lung 174, 1-22.
Mak et al. (1995). Glucocorticosteroids increase beta 2-adrenergic receptor transcription in human lung. American Journal of Physiology 268, L41-L46.
Naline et al. (1994). Relaxant effects and durations of action of formoterol and salmeterol on the isolated human bronchus. European Respiratory Journal 7, 914-920.
EP10781245.5 Extended Search Report dated Jan. 27, 2014.
EP11733493.8 Extended Search Report dated Feb. 27, 2014.
U.S. Appl. No. 12/788,190 Office Action dated Mar. 26, 2014.
U.S. Appl. No. 13/204,423 Office Action dated Apr. 10, 2014.
Wang et al, Preparation of Hydrophobic Drugs Cyclodextrin Complex by Lyophilization Monophase Solution, Drug Development and Industrial Pharmacy, 32:73-83 (2006).
AU2011205646 Examination Report dated Jul. 3, 2014.
CA2,761,744 Examination Report dated Jul. 15, 2014.
Cazzola et al. Novel long-acting bronchodilators for COPD and asthma. Br J Pharmacol. 155(3):291-299 (2008).
CN200680031397.4 Office Action dated Aug. 5, 2014 (w/English translation).
CN201080023277.6 Office Action dated Jul. 7, 2014 (w/English translation).
CN201180056619.9 Office Action dated Jul. 3, 2014 (w/English translation).
EP11844295.3 Extended Search Report dated Nov. 6, 2014.
GB0718905.3 Examination Report dated Feb. 10, 2014.
GB1207749.1 Office Action dated May 13, 2014.
GB1207749 Office Action dated Sep. 19, 2014.
GB1207749.1 Office Action dated Oct. 24, 2014.
GB1120090.4 Office Action dated Oct. 9, 2014.
Greenway et al. Regional Fat Loss from the Thigh in Obese Women after Adrenergic Modulation. Clin. Ther. 9(6): 663-9 (1987).
IL198184 Office Action dated Jun. 30, 2014 (w/English Translation).
JP2009-533423 Office Action dated Jun. 3, 2014 (w/English Translation).
JP2011-083171 Office Action dated May 20, 2014 (w/English translation).
JP2012-095792 Office Action dated Sep. 24, 2014 (w/English Translation).
JP2009-533423 Appeal No. 2012-7183 Trial Decision dated Oct. 28, 2014 (w/English translation).
KR-10-2011-7031166 Notice of Allowance dated May 30, 2014 (w/English Translation).
KR-10-2012-7021302 Office action dated Aug. 21, 2014 (w/English Translation).
KR-2009-7009974 Office Action dated Dec. 6, 2010 (w/English Translation).
MX/a/2009/004198 Office Action dated Jan. 5, 2013 (w/English Translation).
MX/a/2009/004199 Office Action dated Apr. 16, 2012 (w/English Translation).
MX/a/2011/012542 Office Action dated Jun. 12, 2014 (w/English translation).
NCBI PubChem Compound Summary for Isoproterenol. https://pubchem.ncbi.nim.nih.gov/summary/summary.cgi?cid=3779&loc=ex_rcs. Sep. 7, 2014.
NCBI PubChem Compound Summary for Dobutamine/ https://pubchem.ncbi.nim.nih.gov/summary/summary.cgi?cid=36811&loc=rcs. Sep. 4, 2014.

(56) References Cited

OTHER PUBLICATIONS

NCBI PubChem Compound Summary for Salbutamol. https://pubchem.ncbi.nlm.nih.gov/summary/summary.cgi?sid=564130578,viewopt=PubChem. Sep. 16, 2014.
NCBI PubChem Compound Summary for Fluticasone Propionate. https://pubchem.ncbi.nlm.nih.gov/summary/summary.cgi?sid=444036. Sep. 11, 2014.
Schiffelers et al. Lipolytic and nutritive blood flow response to beta-adrenoceptor stimulation in situ in subcutaneous abdominal adipose tissue in obese men. International Journal of Obesity. 27:227-231 (2003).
SG201304014-2 Written Opinion and Search Report dated Jun. 17, 2014 (English Translation only).
Tulloch-Reid et al. Do Measures of Body Fat Distribution Provide Information on the Risk of Type 2 Diabetes in Addition to Measures of General Obesity. Diabetes Care. 26(9): 255661 (Sep. 2003).
U.S. Appl. No. 11/457,436 Office Action dated Aug. 24, 2009.
U.S. Appl. No. 12/788,190 Office Action dated Aug. 14, 2014.
U.S. Appl. No. 13/007,518 Office Action dated Nov. 4, 2014.
U.S. Appl. No. 13/284,741 Response to Non-Final Rejection filed Aug. 17, 2012.
U.S. Appl. No. 13/284,741 Restriction Requirement dated Feb. 17, 2012.
U.S. Appl. No. 13/284,741 Response to Restriction Requirement dated Mar. 13, 2012.
U.S. Appl. No. 13/284,741 Notice of Allowance mailed Jan. 2, 2013.
U.S. Appl. No. 11/457,436 Response to Non-final Rejection dated Oct. 21, 2009.
U.S. 90/013,336 Ex Parte Reexamination filed Sep. 3, 2014.
U.S. 90/013,336 Ex Parte Reexamination filed Sep. 3, 2014, Exhibit A: U.S. Pat. No. 8,420,625.
U.S. 90/013,336 Ex Parte Reexamination filed Sep. 3, 2014, Exhibit B: U.S. Pat. No. 4,525,359, filed by Greenway on Dec. 10, 1982, and issued Jun. 25, 1985.
U.S. 90/013,336 Ex Parte Reexamination filed Sep. 3, 2014, Exhibit C: U.S. Patent Publication No. 2004/0235922, filed by Baile et al. on May 14, 2004, and published on Nov. 25, 2004.
U.S. 90/013,336 Ex Parte Reexamination filed Sep. 3, 2014, Exhibit D: U.S. Patent Publication No. 2005/0113456 filed by Aberg on Nov. 12, 2004, and published on May 26, 2005.
U.S. 90/013,336 Ex Parte Reexamination filed Sep. 3, 2014, Exhibit E: Publication by Linden et al. dated 1996.
U.S. 90/013,336 Ex Parte Reexamination filed Sep. 3, 2014, Exhibit F: U.S. Appl. No. 12/763,030, filed Apr. 19, 2010, now Pub. No. 2011/0105446.
U.S. 90/013,336 Ex Parte Reexamination filed Sep. 3, 2014, Exhibit G: U.S. Appl. No. 11/457,436, filed Jul. 13, 2006, now U.S. Pat. No. 7,829,554.
U.S. 90/013,336 Ex Parte Reexamination filed Sep. 3, 2014, Exhibit H: U.S. Appl. No. 60/732,981, filed Nov. 3, 2005.
U.S. 90/013,336 Ex Parte Reexamination filed Sep. 3, 2014, Exhibit I: U.S. Appl. No. 60/729,531, filed Oct. 24, 2008.
U.S. 90/013,336 Ex Parte Reexamination filed Sep. 3, 2014, Exhibit J: U.S. Appl. No. 60/699,155, filed Jul. 14, 2005.
U.S. 90/013,336 Ex Parte Reexamination filed Sep. 3, 2014, Exhibit K: U.S. Appl. No. 13/096,895 Office Action dated Jun. 26, 2012.
U.S. 90/013,336 Ex Parte Reexamination filed Sep. 3, 2014, Exhibit L: U.S. Appl. No. 13/096,895 Response to Non-Final Office Action dated Dec. 20, 2012.
U.S. 90/013,336 Ex Parte Reexamination filed Sep. 3, 2014, Exhibit M: U.S. Appl. No. 13/096,895 Applicant Initiated Interview Summary dated Jan. 29, 2013.
U.S. 90/013,336 Ex Parte Reexamination filed Sep. 3, 2014, Exhibit N: U.S. Appl. No. 13/096,895 Examiner Initiated Interview Summary dated Feb. 11, 2013.
U.S. 90/013,336 Ex Parte Reexamination filed Sep. 3, 2014, Exhibit O: U.S. Appl. No. 13/096,895 Supplemental Amendment and Response to Interview Summary dated Feb. 8, 2013.
U.S. 90/013,336 Ex Parte Reexamination filed Sep. 3, 2014, Exhibit P: U.S. Appl. No. 13/096,895 Notice of Allowance and Allowability dated Feb. 27, 2013.
U.S. 90/013,336 Ex Parte Reexamination filed Sep. 3, 2014, Exhibit Q: U.S. Appl. No. 12/763,030 Response to Final Office Action dated Jun. 12, 2013.
U.S. 90/013,336 Ex Parte Reexamination filed Sep. 3, 2014, Exhibit R: U.S. Appl. No. 13/096,895 Terminal Disclaimer for U.S. Appl. No. 12/763,030, filed Feb. 7, 2013.
U.S. 90/013,336 Ex Parte Reexamination filed Sep. 3, 2014, Exhibit S: U.S. Appl. No. 12/763,030 Examiner Initiated Interview Summary dated Nov. 13, 2013.
U.S. 90/013,336 Ex Parte Reexamination filed Sep. 3, 2014, Exhibit T: NCBI PubChem Compound Summary for Isoproterenol.
U.S. 90/013,336 Ex Parte Reexamination filed Sep. 3, 2014, Exhibit U, Tulloch-Reid et al. Do Measures of body Fat Distribution Provide Information on the Risk of Type 2 Diabetes in Addition to Measures of General Obesity. Diabetes Care. 26:2556-2561. 2003.
U.S. 90/013,336 Ex Parte Reexamination filed Sep. 3, 2014, Exhibit V: U.S. Appl. No. 60/470,924.
U.S. 90/013,336 Ex Parte Reexamination filed Sep. 3, 2014, Exhibit W: U.S. Appl. No. 60/524,376.
U.S. 90/013,348 Ex Parte Reexamination filed Sep. 19, 2014.
U.S. 90/013,348 Ex Parte Reexamination filed Sep. 19, 2014, Appendix 1.
U.S. 90/013,348 Ex Parte Reexamination filed Sep. 19, 2014, Appendix 2.
U.S. 90/013,348 Ex Parte Reexamination filed Sep. 19, 2014, Appendix 3.
U.S. 90/013,348 Ex Parte Reexamination filed Sep. 19, 2014, Appendix 4.
U.S. 90/013,348 Ex Parte Reexamination filed Sep. 19, 2014, Appendix 5.
U.S. 90/013,348 Ex Parte Reexamination filed Sep. 19, 2014, Exhibit A: U.S. Pat. No. 8,404,750.
U.S. 90/013,348 Ex Parte Reexamination filed Sep. 19, 2014, Exhibit B: European Patent Publication No. EP 0120165.
U.S. 90/013,348 Ex Parte Reexamination filed Sep. 19, 2014, Exhibit C. U.S. Patent Publication No. 2004/0235922.
U.S. 90/013,348 Ex Parte Reexamination filed Sep. 19, 2014, Exhibit D. U.S. Patent Publication No. 2005/0113456.
U.S. 90/013,348 Ex Parte Reexamination filed Sep. 19, 2014, Exhibit E: Publication by Linden et al. Pharmacological Basis for Duration of Effect: Formoterol and Salmeterol Versus Short-Acting 132-Adrenoceptor Agonists. Lung 174:1-22 (1996).
U.S. 90/013,348 Ex Parte Reexamination filed Sep. 19, 2014, Exhibit F: Publication by Schiffelers et al. Lipolytic and nutritive blood flow response to P-adrenoceptor stimulation in situ in subcutaneous abdominal adipose tissue in obese men. International J. of Obesity 27: 227-231 (2003).
U.S. 90/013,348 Ex Parte Reexamination filed Sep. 19, 2014, Exhibit G: U.S. Patent Publication No. 2007/0014843 A1.
U.S. 90/013,348 Ex Parte Reexamination filed Sep. 19, 2014, Exhibit H: U.S. Appl. No. 13/284,741 filed Jul. 13, 2006.
U.S. 90/013,348 Ex Parte Reexamination filed Sep. 19, 2014, Exhibit I: U.S. Appl. No. 12/788,190 filed May 26, 2010.
U.S. 90/013,348 Ex Parte Reexamination filed Sep. 19, 2014, Exhibit J: U.S. Appl. No. 61/181,627.
U.S. 90/013,348 Ex Parte Reexamination filed Sep. 19, 2014, Exhibit K: U.S. Appl. No. 61/251,624.
U.S. 90/013,348 Ex Parte Reexamination filed Sep. 19, 2014, Exhibit L: U.S. Appl. No. 61/289,972.
U.S. 90/013,348 Ex Parte Reexamination filed Sep. 19, 2014, Exhibit M: U.S. Appl. No. 13/284,741 Non-final Rejection mailed May 17, 2012.
U.S. 90/013,348 Ex Parte Reexamination filed Sep. 19, 2014, Exhibit N: U.S. Appl. No. 13/284,741 Response to Non-final Rejection dated Aug. 17, 2012.
U.S. 90/013,348 Ex Parte Reexamination filed Sep. 19, 2014, Exhibit 0: U.S. Appl. No. 13/284,741 Restriction Requirement mailed Feb. 17, 2012.

(56) References Cited

OTHER PUBLICATIONS

U.S. 90/013,348 Ex Parte Reexamination filed Sep. 19, 2014, Exhibit P: U.S. Appl. No. 13/284,741 Response to Restriction Requirement dated Mar. 13, 2012.
U.S. 90/013,348 Ex Parte Reexamination filed Sep. 19, 2014, Exhibit Q: U.S. Appl. No. 13/284,741 Notice of Allowance mailed Jan. 2, 2013.
U.S. 90/013,348 Ex Parte Reexamination filed Sep. 19, 2014, Exhibit R: U.S. Appl. No. 11/457,436.
U.S. 90/013,348 Ex Parte Reexamination filed Sep. 19, 2014, Exhibit S: U.S. Pat. No. 7,829,554.
U.S. 90/013,348 Ex Parte Reexamination filed Sep. 19, 2014, Exhibit T. U.S. Appl. No. 11/457,436 Non-final Rejection mailed Aug. 24, 2009.
U.S. 90/013,348 Ex Parte Reexamination filed Sep. 19, 2014, Exhibit U: Response to Non-final Rejection dated Oct. 21, 2009.
U.S. 90/013,348 Ex Parte Reexamination filed Sep. 19, 2014, Exhibit V: NCBI PubChem Compound Summary for Isoproterenol.
U.S. 90/013,348 Ex Parte Reexamination filed Sep. 19, 2014, Exhibit W: Publication by Frank L. Greenway and George A Bray. Regional Fat Loss from the Thigh in Obese Women after Adrenergic Modulation. Clin. Ther. 9(6): 663-9 (1987).
U.S. 90/013,348 Ex Parte Reexamination filed Sep. 19, 2014, Exhibit X. Publication by Marshall K. Tulloch-Reid et al. Do Measures of Body Fat Distribution Provide Information on the Risk of Type 2 Diabetes in Addition to Measures of General Obesity. Diabetes Care. 26(9): 255661 (Sep. 2003).
U.S. 90/013,348 Ex Parte Reexamination filed Sep. 19, 2014, Exhibit Y: NCBI PubChem Compound Summary for Dobutamine.
U.S. 90/013,348 Ex Parte Reexamination filed Sep. 19, 2014, Exhibit Z: NCBI PubChem Compound Summary for Salbutamol.
U.S. 90/013,348 Ex Parte Reexamination filed Sep. 19, 2014, Exhibit AA: NCBI PubChem Compound Summary for Fluticasone Propionate.
CA 2,761,744 Examination Report dated Dec. 28, 2012.
CN200780046741.1 Office Action dated Aug. 8, 2013 (English translation only).
KR-10-2011-7031166 Office Action dated Jul. 17, 2013 (English translation only).
PCT/US2011/061972 International Preliminary Report on Patentability and Written Opinion dated May 28, 2013.
PCT/US2011/061973 International Preliminary Report on Patentability and Written Opinion dated May 28, 2013.
Schwegman et al., "Practical Formulation and Process Development of Freeze-Dried Products," Pharmaceutical Development and Technology 10:151-173 (2005).
Teagarden et al., "Practical aspects of lyophilization using non-aqueous co-solvent systems," Eur J. Pharm Sci., 15(2):115-33 (2002).
U.S. Appl. No. 12/788,190 Office Action dated May 8, 2013.
U.S. Appl. No. 13/007,518 Office Action dated Aug. 5, 2013.
AU2011205646 Examination Report dated Jan. 7, 2013.
CA 2,786,618 Examination Report dated May 21, 2013.
CN 200680031397.4 Office Action dated Jan. 25, 2013 (English translation only).
CN 200780046741.1 Office Action dated Nov. 20, 2012 (English translation only).
CN 201080023277.6 Office Action dated Dec. 26, 2012 (English translation only).
CN201180013558.8 Office Action dated May 28, 2013 (English translation only).
EA 201270683/26 Office Action dated Dec. 5, 2012 (English translation only).
EP07843370 Extended Search Report mailed Feb. 26, 2010.
Finney et al., Chronic systemic administration of salmeterol to rats promotes pulmonary beta(2)-adrenoceptor desensitization and down-regulation of G(s alpha), Br. J. Pharmacol., vol. 132, No. 6, pp. 1261-1270 (2001).
GB 1120090.4 Search and Examination Report mailed Dec. 9, 2011.
GB 1120091.2 Search and Examination Report mailed Dec. 9, 2011.
GB1008885.4 Examination Report dated Jan. 8, 2013.
Hoffman, et al., "Clenbuterol ingestion causing prolonged tachycardia, hypokalemia, and hypophosphatemia with confirmation by quantitative levels," J. of Toxicology, Clinical Toxicology, 2001, 39(4), 339-344.
IL 198184 Office Action dated Jan. 20, 2013 (English translation only).
JP 2011083171 Office Action dated Mar. 21, 2013 (English translation only).
Kim et al., "Prevention and reversal of pulmonary inflammation and airway hyperresponsiveness by dexamethasone treatment in a murine model of asthma induced by house dust," Am. J. Physiol Lung Cell Mol Physiol., vol. 287, No. 3, pp. L503-L509 (2004).
MX/A/2009/004198 Exam Report dated May 29, 2012 (English translation only).
MX200800570 Office Action dated Nov. 18, 2011 (English translation only).
PCT/US10/36484 Search Rpt & Written Opn. Mailed Feb. 21, 2011.
Ryall et al., "Intramuscular beta2-agonist administration enhances early regeneration and functional repair in rat skeletal muscle after myotoxic injury," Journal of Applied Physiology, 2008, vol. 105, pp. 165-172.
SG 201108652-7 Search Report dated Mar. 4, 2013 (English translation only).
U.S. Appl. No. 12/445,570 Office Action dated Mar. 6, 2013.
U.S. Appl. No. 13/204,423 Office Action dated Dec. 5, 2012.
AU2007313077 Exam Report dated Jan. 29, 2010.
AU2007313077 Exam Report dated Oct. 13, 2010.
AU2010253864 Examiner's Report dated Sep. 17, 2013.
AU2007325523 Examination Report dated Mar. 24, 2010.
Bray et al, Current and Potential Drugs for Treatment of Obesity, Endocrine Reviews, 20(6):805-875 1999.
CA 2,615,173 Examination Report dated Mar. 31, 2011.
CA 2,615,173 Examination Report dated Sep. 21, 2010.
CA 2,666,612 Office Action dated Nov. 9, 2010.
CA 2,666,564 Examination Report dated Oct. 19, 2010.
CN0780046201.3 Office Action dated Oct. 11, 2010 (w/English Translation).
CN200680031397.4 Office Action dated Dec. 27, 2013 (w/English Translation).
CN200780046741.1 Office Action dated Dec. 3, 2013 (w/English translation).
CN200780046741.1 Office Action dates Feb. 23, 2011 (w/English translation).
Ding et al, Modulation of porcine adipocyte beta-adrenergic receptos by a beta-adrenergic agonist, J. of Animal Science, Apr. 2000, 78(4):919-926.
EP06787329.9 Office Action dated May 26, 2011.
EP07843370.3 Office Action dated Jan. 14, 2011.
EP07843370.3 Office Action dated Mar. 27, 2012.
EP07843370.3 Office Action dated Sep. 19, 2011.
EP07871172.8 Exam Report dated Sep. 8, 2010.
EP11180982.8 Exam Report dated Oct. 16, 2013.
GB0804401.8 Examination Report dated Aug. 21, 2009.
GB1008885.4 Exam Report dated Jul. 26, 2011.
GB1008885.4 Exam Report dated Sep. 19, 2012.
GB1120090.4 Office Action dated Nov. 29, 2013.
IL198184 Office Action dated Apr. 22, 2010 (English translation only).
Johnson, M., "Pharmacology of long-acting β-agonists," Annals of Allergy Asthma & Immunology: Official Publication of the American College of Allergy, Asthma & Immunology, Aug. 1995, vol. 75, No. 2, pp. 177-179, ISSN: 1081-1206.
JP2009-234928 Office Action dated Nov. 1, 2010 (w/English Translation).
JP2008-521686 Office Action dated Jan. 4, 2011 (English Translation only).
JP2009-533423 Office Action dated Nov. 16, 2010 (w/English translation).
JP2012-513273 Office action dated Oct. 29, 2013 (w/English Translation).
KR-10-2009-7009972 Office Action dated Aug. 22, 2011 (w/English translation).

(56) References Cited

OTHER PUBLICATIONS

KR-10-2012-7021302 Office action dated Nov. 19, 2013 (w/English translation).
KR-2009-7009974 Office Action dated Jun. 1, 2011 (w/English translation).
MX/a/2011/012542 office action dated Nov. 15, 2013 (w/English Translation).
PCT/US2006/027405 International Preliminary Report on Patentability date Jan. 16, 2008.
PCT/US2007/079740 International Preliminary Report on Patentability date Apr. 22, 2009.
PCT/US2007/081568 International Preliminary Report on Patentability date Apr. 22, 2009.
PCT/US2011/061973 International Search Report dated Dec. 28, 2012.
SG 201108652-7 Search Report dated Nov. 6, 2013 (English translation only).
SG201205142-1 Search Report and Written Opinion dated Oct. 29, 2013 (English Translation only).
Tomioka, K. et al., "Effects of Formoterol (BD 40A), a β-Adrenocepto Stimulant, on Isolated Guinea-Pig Ling Parenchymal Strips and Antigen-Induced SRS-A Release in Rats," Archives Internationales De Pharmacodynamie Et De Therapie, Jan. 1984, vol. 267, No. 1, pp. 91-102: ISSN:0003-9780.
U.S. Appl. No. 12/445,570 Office action dated Dec. 26, 2013.
U.S. Appl. No. 13/007,518 Office Action dated Jan. 24, 2014.
U.S. Appl. No. 13/204,423 Office Action dated Dec. 13, 2013.
Yang, et al. "Multiple actions of β-adrenergic agonists on skeletal muscle and adipose tissue." Biochem. J. (1989) 261, 1-10.
CA2,786,618 Examination Report dated Jan. 16, 2015.
CN200680031397.4 Office Action dated May 23, 2013 (w/English translation).
CN201080023277.6 Office Action dated Oct. 15, 2013 (w/English translation).
CN201180013558.8 Office Action dated Nov. 13, 2014 (w/English Translation).
Dalyrmple et al. A repartitioning agent to improve performance and carcass composition of broilers. Poult Sci 63(12):2376-2383 (1984).
Declaration of Dr. Kenneth Locke together with CV and data exhibits dated Feb. 24, 2014.
Drugs in Japan. Japan Drug Information Center. pp. 882-884 (2004 Ed.) (w/Partial English Translation).
EP06787329.9 Decision Rejecting Opposition dated Feb. 5, 2015.
GB1120090.4 Office Action dated Jan. 19, 2015.
Hamano et al. Combined effects of clenbuterol and various concentrations of protein on performance of broiler chickens. Br Poul Sci 39:117-122 (1998).
Human Genome Sciences Inc. v Eli Lilly and Company UKSC 51 [2011].
IL216217 Office Action date Dec. 3, 2014 (English Only).
JP2009-533423 Office Action dated Aug. 2, 2011 (w/English translation).
JP2011-083171 Pre-Appeal Examination Report dated Dec. 19, 2014 (w/English translation).
JP2012-513273 Office Action dated Nov. 20, 2014 (w/English Translation).
JP2012-549145 Office Action dated Nov. 12, 2014 (w/English Translation).
KR-10-2009-7009972 Office Action dated Dec. 6, 2010 (w/English Translation).
Letter written by Professor Frank Greenway, M.D. to Dr. John Dobak, M.D., dated May 12, 2010.
Med. Pract. 22(4):611-615 (2005) (w/Partial English Translation).
MX/a/2008/000570 Office Action dated Jan. 21, 2013 (w/English Translation).
MX/a/2008/000570 Office Action dated Nov. 18, 2011 (w/English Translation).
MX/a/2008/000570 Office Action dated Apr. 7, 2011 (w/English Translation).
MX/a/2011/012542 Notice of Allowance dated Dec. 16, 2014 (w/English Translation).
MX/a/2011/012542 Office Action dated Apr. 10, 2013 (w/English Translation).
MX/a/2011/012542 Office Action dated Jul. 15, 2013 (w/English Translation).
NEMA et al. Encyclopedia of Pharmaceutical Technology pp. 1622-1645 (2007).
NZ2011336869 Office Action dated Feb. 13, 2015.
Rehfeldt et al. Effect of clenbuterol on growth, carcase and skeletal muscle characteristics in broiler chickens. Br Poul Sci 38:366-373 (1997).
Strickley. Solubilizing excipients in oral and injectable formulations. Pharm Res. 21(2):201-230 (2004).
U.S. Appl. No. 13/204,423 Office Action dated Dec. 15, 2014.
U.S. Appl. No. 13/303,045 Office Action dated Dec. 11, 2014.
U.S. Appl. No. 12/788,190 Office Action dated Mar. 4, 2015.
Zhou et al. Effects of dietary supplementation of beta 2-adrenergic agonist clenbuterol on carcase characteristics and some metabolites in ducks. Br Poul Sci 35:355-361 (1994).
CN200680031397.4 Office Action dated Feb. 4, 2015 (w/English translation).
KR10-2012-7021302 Office Action dated Feb. 24, 2015 (w/English Translation).
SG201304014-2 Written Opinion dated Feb. 2, 2015.
U.S. Appl. No. 90/013,348 Office Action dated Mar. 23, 2015.
CN201180056619.9 Office Action dated Dec. 1, 2015 (w/English translation).
EP10781245.5 Office Action dated Dec. 15, 2015.
JP2014-052975 Office Action dated Nov. 17, 2015 (w/English translation).
PCT/US2015/052248 International Search Report and Written Opinion dated Dec. 22, 2015.
AU2011336869 Office Action dated Apr. 16, 2015.
CA2,761,744 Office Action dated Apr. 1, 2015.
CN201080023277.6 Office Action dated Apr. 8, 2015 (w/English Translation).
CN20118001355.8 Office Action dated Jun. 2, 2015 (w/English Translation).
CN201180056619.9 Office Action dated Mar. 18, 2015 (w/ English Translation).
Co-pending U.S. Appl. No. 14/812,993, filed Jul. 29, 2015.
Co-pending U.S. Appl. No. 14/835,587, filed Aug. 25, 2015.
IL198184 Notice of Allowance dated Mar. 16, 2015. (w/English Translation).
IL220818 Office Action dated Apr. 29, 2015.
JP2012-095792 Office Action dated May 19, 2015 (w/English Translation).
JP2012-549145 Office Action dated Apr. 13, 2015 (w/English Translation).
JP2014-038412 Office Action dated Feb. 12, 2015 (w/English Translation).
JP2014-052975 Office Action dated Feb. 13, 2015 (w/English Translation).
KR10-2012-7021302 Office Action date Apr. 17, 2015 (w/English Translation).
U.S. Appl. No. 12/763,030 Office Action dated May 18, 2015.
U.S. Appl. No. 13/007,518 Office Action dated Jun. 30, 2015.
U.S. Appl. No. 13/096,895 Office Action dated Jun. 26, 2012.
U.S. Appl. No. 13/303,045 Office Action dated Jun. 2, 2015.
U.S. Appl. No. 90/013,336 Ex Parte Communication and Notice of Intent to Issue Ex Parte Reexamination Certificate dated Jul. 31, 2015.
U.S. Appl. No. 90/013,336 Ex Parte Reexamination Interview Summary dated May 12, 2015.
U.S. Appl. No. 90/013,348 Ex Parte Communication and Notice of Intent to Issue Ex Parte Reexamination Certificate dated Jul. 31, 2015.
U.S. Appl. No. 90/013,348 Ex Parte Reexamination Interview Summary dated May 12, 2015.

(56) References Cited

OTHER PUBLICATIONS

Ascher et al. Efficacy, patient-reported outcomes and safety profile of ATX-101 (deoxycholic acid), an injectable drug for the reduction of unwanted submental fat: results from a phase III, randomized, placebo-controlled study. J Eur Acad Dermatol Venereol 28(12):1707-1715 (2014).

Ascher et al. Patient-reported outcomes from a second European phase III clinical trial of ATX-101, an injectable agent for the reduction of submental fat. 15th Annual Congress of the International Master Course on Aging Skin (IMCAS), Paris, France, Jan. 31-Feb. 3, 2013 15th Annual Congress of the International Course on Aging Skin (IMCAS), Paris, France, Jan. 31-Feb. 3, 2013.

CN200680031397.4 Office Action dated Sep. 2, 2015 (w/English translation).

Co-pending U.S. Appl. No. 14/866,471, filed Sep. 25, 2015.

JP2013-541034 Office Action dated Sep. 24, 2015 (w/English translation).

JP2015-143281 Office Action dated Oct. 7, 2015 (English only).

KR10-2015-7018454 Office Action dated Sep. 14, 2015 (w/English translation).

Krochmal et al. Aesthetic Treatment of Central Abdominal Bulging (CAB) with LIP-202 (Salmeterol Xinafoate for Injection). J of Derm Clin Res 7 pgs (2015).

McDiarmid et al. Results from a Pooled Analysis of Two European, Randomized, Placebo-Controlled, Phase 3 Studies of ATX-101 for the Pharmacologic Reduction of Excess Submental Fat. Aesth Plast Surg 38(5):849-860 (2014).

MX/a/2012008171 Office Action dated Sep. 2, 2015 (w/English translation).

New Pharmacology. 4th ed. pp. 10-11 (2002) (Japanese only).

Sterile Water (Water) Injection, Solution, Hospira Mar. 2007.

TW100142782 Office Action dated Aug. 25, 2015 (w/English translation).

U.S. Appl. No. 12/445,570 Office Action dated Oct. 2, 2015.

KR10-2015-7018454 Office Action dated Feb. 1, 2016 (w/English translation).

Sagara. Right and wrong of salmeterol/fluticasone propionate combination. Arerugi 55(7):794-810 (2007 (English Abstract).

U.S. Appl. No. 13/303,045 Office Action dated Apr. 6, 2016.

U.S. Appl. No. 14/835,587 Office Action dated Feb. 8, 2016.

\* cited by examiner

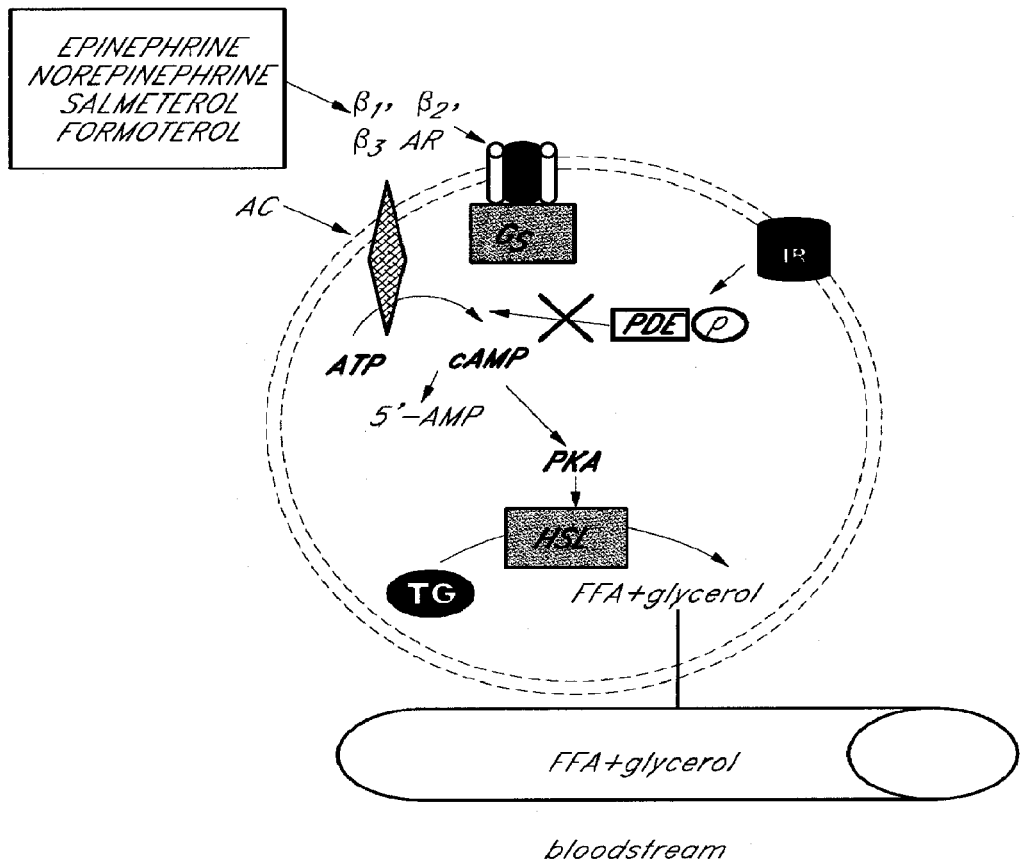

METHODS OF USING LIPOLYTIC FORMULATIONS FOR REGIONAL ADIPOSE TISSUE TREATMENT

CROSS-REFERENCE TO RELATED APPLICATIONS

This application claims the benefit under 35 U.S.C. §121 of U.S. application Ser. No. 11/457,436 filed Jul. 13, 2006 which claims benefit to U.S. Provisional Application Nos. 60/699,155 filed Jul. 14, 2005, 60/729,531 filed Oct. 24, 2005, and 60/732,981 filed Nov. 3, 2005; each application to which the instant application claims the benefit of is hereby incorporated by reference in its entirety.

BACKGROUND OF THE INVENTION

1. Field of the Invention

This disclosure relates generally to medical treatment, and more particularly to the treatment of fat deposits.

2. Description of the Related Art

Adipose tissue is the primary energy storage tissue of the body. Fat cells, or adipocytes, store this energy in the form of triglycerides. Triglycerides are mobilized from fat stores to provide caloric energy to the body through hormonal induction of triglyceride hydrolysis. This process releases free or non-esterified fatty acids and glycerol into the blood for use by other body tissues. The breakdown of triglycerides from fat store is referred to as lipolysis. Growth of new adipocytes also occurs, which is referred to as adipogenesis.

Weight loss programs involving exercise can stimulate lipolysis through adrenergic stimulation resulting in fat reduction. Primary hormones and neurotransmitters that control lipolysis in the body are the catecholamines. Adipose tissue has beta-1, 2, and 3 adrenergic receptors and alpha-2 adrenergic receptors. Binding of beta agonists to beta receptors in adipose tissue can result in adipocyte lipolysis, while binding of alpha receptor agonists can inhibit lipolysis. Beta receptor activation can also inhibit adipogenesis. In humans, the beta-2 receptor are often the most abundant on fat cell surfaces and the primary mediator of beta receptor-stimulated lipolysis. Stimulation of lipolysis by beta agonists is mediated by adenylate cyclase and increased formation of cyclic adenosine monophosphate (cyclic AMP, cAMP).

Accumulation of fat stores can occur unevenly in the body. For example, persons may accumulate fat predominantly in the abdominal cavity while others predominately in the subcutaneous tissue. Gender differences may also be apparent with women accumulating fat in the thighs and lateral buttocks and males in the waist. Women may accumulate fatty deposits of the thighs, which have a rumpled or "peau-de-orange" appearance, resulting in a condition referred to as cellulite. Cellulite may be related to skin architecture which allows subdermal fat herniation, sometimes referred to as adipose papillae. Other factors that may be related to cellulite include altered and/or reduced connective tissue septae, vascular and lymph changes that lead to fluid accumulation, and inflammation. Fat tissue may also accumulate in the form of a fibrous fatty deposit known as a lipoma.

Similarly, utilization of fat stores may occur unevenly. Persons who have lost substantial weight may still have regional pockets of fat accumulation that are resistant to reduction unless unhealthy extremes of weight loss are achieved. Exercise may affect subcutaneous fat stores differently, with deeper tissues responding with lipolysis and superficial stores being more resistant. Cellulite may also still be present despite weight loss, and lipomas are typically not affected by weight loss.

Differential utilization of fat stores may be in part due to the action of adrenergic receptors. Thus, certain regions may have higher alpha-2 receptor activity or a higher number of alpha-2 receptors relative to beta-2 receptors, leading to a reduction of lipolysis. Studies have shown a difference in lipolytic activity in response to beta adrenergic receptor stimulation in adipose tissue of the omentum versus the subcutaneous abdomen versus the thigh, with the omentum having the highest activity and the thigh having the lowest activity. The differences in lipolytic activity can be abolished by the addition of an alpha-2 receptor antagonist, suggesting that excessive alpha-2 receptor activities is a cause for lower lipolytic response to adrenergic stimulation in different adipose tissue regions.

Delivery of adrenergic active ingredients into the subcutaneous tissue, both beta agonists and alpha-2 antagonists, has been proposed and has been shown to result in regional fat loss and improved appearance of regional fat accumulations. For example, isoproterenol 11 and yohimbine 8 have been shown to reduce the thigh circumference in women. These studies required subcutaneous injections of beta agonists three to five times per week in multiple locations over the thighs. This is not practical as a commercially viable product for regional fat loss and would cause significant discomfort to the patient. Because these lipolytic agents, especially the beta agonists, are short-acting and may be rapidly removed from the adipose tissue, the lipolysis is likely to have occurred for only a short time after the injection thereby reducing the potential magnitude of the effect despite the multiple injections. Additionally, long term exposure of adipocytes to beta agonists results in receptor desensitization and down regulation, and a loss of lipolytic activity. Means to reduce or prevent these effects on the receptor may also improve the therapy.

SUMMARY OF THE INVENTION

Compositions, formulations, methods, and systems for treating regional fat deposits comprise contacting a targeted fat deposit with a composition comprising long acting beta-2 adrenergic receptor agonist and a compound that reduces desensitization of the target tissue to the long acting beta-2 adrenergic receptor agonist, for example, glucocorticosteroids and/or ketotifen. Embodiments of the composition are administered, for example, by injection, and/or transdermally.

Some embodiments provide an injectable formulation for adipose tissue accumulation comprising: a long acting selective beta-2 adrenergic receptor agonist; a compound for reducing desensitization of adipose tissue to a beta-adrenergic receptor agonist; and a liquid carrier.

In some embodiments, the long acting selective beta-2 adrenergic receptor agonist is lipophilic. In some embodiments, the long acting selective beta-2 adrenergic receptor agonist comprises at least one of salmeterol, formoterol, salts thereof, and solvates thereof.

In some embodiments, the compound for reducing desensitization of the target tissue to a beta-adrenergic receptor agonist comprises a glucocorticosteroid. In some embodiments, the compound for reducing desensitization of the target tissue to a beta-adrenergic receptor agonist comprises an antihistamine. In some embodiments, the compound for reducing desensitization of the target tissue to a beta-adrenergic receptor agonist comprises a glucocorticosteroid and an antihistamine. In some embodiments, the compound for reducing desensitization of the target tissue to a beta-adrenergic receptor agonist comprises at least one of dexamethasone, prednisolone, fluticasone proprionate, budesonide, ketotifen, and analogs thereof.

In some embodiments, the liquid carrier comprises a lipophilic liquid carrier.

In some embodiments, at least one of the long acting selective beta-2 adrenergic receptor agonist and the compound for reducing desensitization is loaded on a sustained release agent. In some embodiments, the sustained release agent comprises at least one of a biodegradable polymer, a biodegradable copolymer, a hydrogel, and a liposome. In some embodiments, the sustained release agent comprises poly (lactide glycolide). In some embodiments, an active ingredient loading on the poly(lactide glycolide) is up to about 75%.

Some embodiments comprise at least one of salmeterol, a salt thereof, and a solvate thereof; and fluticasone.

Some embodiments comprise at least one of formoterol, a salt thereof, and a solvate thereof; and budesonide. Some embodiments comprise at least one of salmeterol, formoterol, salts thereof, and solvates thereof; and ketotifen.

Other embodiments provide an injectable formulation for treating fat accumulation comprising: at least one long acting selective beta-2 adrenergic receptor agonist; a means far reducing desensitization of the target tissue to a beta-adrenergic receptor agonist; and a liquid carrier. In some embodiments, the at least one long acting selective beta-2 adrenergic receptor agonist comprises at least one of salmeterol, formoterol, salts thereof, and solvates thereof.

Other embodiments provide a method for treating a fat accumulation comprising: contacting a fat accumulation with a pharmaceutically effective amount of a long acting selective beta-2 adrenergic receptor agonist; and contacting a fat accumulation with a pharmaceutically effective amount of a compound for reducing desensitization of the target tissue to a beta-adrenergic receptor agonist.

In some embodiments, the long acting selective beta-2 adrenergic receptor agonist comprises at least one of salmeterol, formoterol, salts thereof, and solvates thereof.

In some embodiments, the compound for reducing desensitization of the target tissue to a beta-adrenergic receptor agonist comprises at least one of a glucocorticosteroid, dexamethasone, prednisolone, fluticasone proprionate, budesonide, and ketotifen.

In some embodiments, at least one of the long acting selective beta-2 adrenergic receptor agonist and the compound for reducing desensitization is loaded on a sustained release agent.

In some embodiments, the long acting selective beta-2 agonist comprises salmeterol and the pharmaceutically effective amount of salmeterol is up to about 100 µg/day. In some embodiments, the long acting selective beta-2 agonist comprises formoterol and the pharmaceutically effective amount of formoterol is up to about 50 µg/day.

In some embodiments, the long acting selective beta-2 adrenergic receptor agonist and the compound for reducing desensitization are delivered substantially simultaneously. In some embodiments, at least one of the long acting selective beta-2 adrenergic receptor agonist and the compound for reducing desensitization is delivered by single needle injection. In some embodiments, at least one of the long acting selective beta-2 adrenergic receptor agonist and the compound for reducing desensitization is delivered by needleless injection. In some embodiments, at least one of the long acting selective beta-2 adrenergic receptor agonist and the compound for reducing desensitization is delivered transdermally.

Other embodiments provide a method for reducing adipose tissue comprising: administering a pharmaceutically effective amount of a compound, wherein the compound increases beta-2 adrenergic receptors in a region of adipose tissue; and administering a pharmaceutically effective amount of a selective long acting beta-2 receptor agonist to the region of adipose tissue, thereby resulting in the region of adipose tissue exhibiting at least one of lipolysis and inhibited adipogenesis.

In some embodiments, at least one of the administering the compound and the administering the beta-2 receptor agonist is performed less frequently than once per day.

Other embodiments provide a method for treating regional fat accumulations or cellulite comprising: administering to a regional fat accumulation or cellulite a composition comprising: a long acting selective beta-2 agonist; and at least one of a glucocorticosteroid and ketotifen, wherein the composition exhibits sustained lipolytic activity thereby promoting lipolysis in the regional fat accumulation or cellulite.

In some embodiments, the long acting selective beta-2 agonist comprises at least one of salmeterol, formoterol, salts thereof, and solvates thereof.

Some embodiments provide a controlled release formulation comprising a controlled release carrier, a long acting selective beta-2 adrenergic receptor agonist, and a glucocorticosteroid. The controlled release carrier reduces fat in the treatment of regional fat accumulation. In some embodiments, the long acting selective beta-2 agonist is salmeterol and/or formoterol. In some embodiments, the controlled release carrier is a biodegradable polymer. In some embodiments, the biodegradable polymer is comprises lactide and glycolide. In some embodiments, the biodegradable polymer is formulated as a microparticle. In some embodiments, the glucocorticoid is fluticasone, budesonide, and/or dexamethasone. In some embodiments, at least a portion of the formulation is delivered to the fat accumulation through a needleless injection device. In additional embodiments, the needleless injection device promotes the lateral spread of the formulation in the fat accumulation.

Some embodiments provide a method for reducing adipose tissue by treating a region of fat involves the administration of pharmacologically effective amounts of a glucocorticosteroid or ketotifen to a region of fat. The glucocorticosteroid or ketotifen increases the beta-2 adrenergic receptors on the adipocytes in the fat region, thereby improving the lipolytic activity and/or adipogenesis inhibition of a co-administered selective long acting beta-2 receptor agonist to the regional fat accumulation.

In some embodiments, the long acting selective beta-2 agonist is salmeterol. In some embodiments, the pharmacologically effective amount of salmeterol is up to about 100 micrograms per day. In some embodiments, the long acting selective beta-2 agonist is formoterol In some embodiments, the pharmacologically effective amount of formoterol is up to about 50 micrograms per day.

Some embodiments provide a method for treating a region of fat comprising administering a pharmacologically effective formulation comprising a lipophilic, substantially selective beta-2 receptor agonist with sustained adrenergic activity in adipose tissue, thereby causing sustained lipolysis. Some embodiments of the method further comprise co-administering a glucocorticosteroid or ketotifen to further sustain and enhance lipolysis. Some embodiments of the method further comprise administering the formulation less than once each day.

Some embodiments provide a method for treating regional fat accumulations or cellulite comprising administering a composition comprising a long acting substantially selective beta-2 agonist, and a glucocorticosteroid or ketotifen. Embodiments of the method promote lipolysis in resistant fat tissue and exhibit sustained lipolytic activity, thereby reducing regional fat accumulation and improving the appearance of cellulite.

BRIEF DESCRIPTION OF THE DRAWINGS

FIG. 1 schematically illustrates adipocyte lipolysis.

DETAILED DESCRIPTION OF THE PREFERRED EMBODIMENT

Embodiments of pharmaceutical compositions, formulations, methods, and systems achieve regional fat, adipose tissue, and adipocyte reduction therapy through adrenergic system modulation. As used and/or cited herein, the term "modulation" is generally used in its usual sense, and more particularly to refer to adrenergic receptor agonism, adrenergic receptor antagonism, and/or changes in receptor signaling pathways. One example of a change in receptor signaling pathways includes an increase in cyclic AMP, for example as illustrated schematically in FIG. 1. In some embodiments, modulation refers to receptor upregulation or an increase in the number of adrenergic receptors, a decrease in receptor deactivation or sequestration, receptor activity changes (for example, an increase in activity), and/or changes in receptor affinity.

It is believed that some embodiments of sustained modulation of adrenergic receptors in adipose tissue result in some combination of sustained lipolysis, reduced lipid content of the adipocyte, reduced adipocyte cell size, reduced adipose tissue mass or fat accumulation, and/or improved cosmetic appearance. Some embodiments provide selective reduction of regional and/or subcutaneous accumulations of adipose tissue and adipocytes, including cellulite, through sustained adrenergic modulation. Sustained adrenergic modulation result in sustained inhibition of fat cell proliferation (adipogenesis) in some embodiments. In some embodiments, the composition is useful for treating cellulitic fat accumulation and/or lipomas.

Embodiments of the disclosed pharmaceutical compositions comprise one or more long acting selective beta-2 adrenergic receptor agonists in combination with one or more compounds that reduce desensitization of the target tissue to the beta-adrenergic receptor agonist(s), for example, glucocorticosteroids or ketotifen, or analogs thereof. The term desensitization includes both short term desensitization (tachyphylaxis), as well as long term desensitization, as well as desensitization over other time periods. Beta-2 adrenergic receptor agonists are also referred to herein as "beta-2 agonists" and "beta-2 receptor agonists." Unless otherwise specified, references to beta-2 adrenergic receptor agonists also include their analogs, physiologically acceptable salts and/or solvates known in the art. Some embodiments of the composition comprise from about 100:1 to about 1:100 long-acting selective beta-2 agonist to glucocorticosteroid.

As discussed above, lipolytic activity and adipocyte proliferation inhibition are believed to be mediated through modulation of adrenergic receptors in adipose tissue and/or on adipocytes. In some embodiments, the reduction therapy is enhanced through prolonged exposure or sustained activity of one or more adrenergic receptor agonists and/or receptor pathway stimulating compounds known in the art, for example, catecholamines, beta agonists, alpha antagonists, forskolin, aminophylline, analogs thereof, or combinations thereof.

Some embodiments provide sustained adrenergic modulation through the use of pharmaceutical compositions comprising one or more long-acting substantially selective beta-2 receptor agonists. Some embodiments of the sustained activity pharmaceutical composition comprise one or more suitable long-acting, selective beta-2 agonists known in the art, for example, salmeterol 1, formoterol 2, bambuterol 3, physiologically acceptable salts or solvates thereof, or combinations thereof.

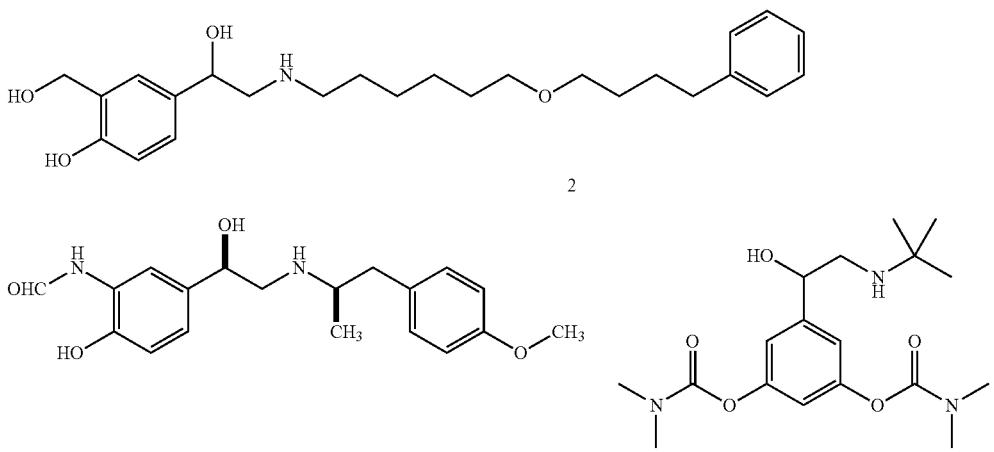

Sustained adrenergic modulation is not observed in the subcutaneous delivery of typical adrenergic compositions because the adrenergic compound is generally rapidly removed from the adipose tissue through the blood and/or lymph. Furthermore, long-term exposure of adipose tissue to adrenergic agents, particularly beta receptor agonists, is believed to result in receptor desensitization through receptor phosphorylation and sequestration. It is believed that these effects limit the ability of an adrenergic modulating composition to treat adipose tissue and result in tachyphylaxis, a condition in which the body experiences a rapidly decreasing response to the agonist following administration of the initial doses, to the desired lipolytic and anti-adipogenesis effect. Consequently, the treatment effect is short lived and frequent dosing is required.

Short-acting beta-2 agonists often result in tachyphylaxis, as discussed above. However, because preferred embodiments of long-acting selective beta-2 agonists have substantially selective beta-2 receptor activity and high lipophilicity, the activities of long-acting beta-2 agonists continue for longer periods of time in adipose tissue compared with short-acting beta-2 agonists. Partial beta-2 receptor antagonist activity prevents desensitization that can occur with continuous exposure of adipocytes to full adrenergic agonists. Consequently, long-acting selective beta-2 agonists exhibit a reduced tachyphylaxis. Compared with short-acting beta-2 agonists, lipolysis also occurs for a longer time after administration because long-acting selective beta-2 agonists have longer half-lives. The combination of longer half-lives and activities reduces the frequency of administration of the pharmaceutical compositions. Consequently, in some embodiments, daily administration of the composition is not required. Moreover, preferred embodiments of long-acting selective beta-2 agonists also exhibit greater selectivity for beta-2 receptors, permitting substantially similar therapeutic effects compound with short-acting beta-2 agonists at a lower dosage.

As discussed above, lipolysis and/or inhibition of adipogenesis are stimulated by the beta-1, 2, or 3 receptor subtypes. Thus, agonists to one, two and/or all three receptors are capable of stimulating lipolysis and/or inhibition of adipogenesis. In humans, beta-2 receptor activity is believed to be more important fox stimulating lipolysis, particularly in the presence of an anti-inflammatory steroid or glucocorticosteroid.

Long-acting selective beta-2 agonists, for example, salmeterol 1 (±2-(hydroxymethyl)-4-[1-hydroxy-2-[6-(4-phenylbutoxy)hexylamino]ethyl]-phenol, CAS Reg. No. 94749-08-3), and formoterol 2 (±N-[2-hydroxy-5-[1-hydroxy-2-[1-(4-methoxyphenyl)propan-2-ylamino]ethyl]-phenyl] methanamide, CAS Reg. No. 73573-87-2), are preferred in some embodiments. Some embodiments of the compositions comprise one or more long-acting selective beta-2 agonists as physiologically acceptable salts or solvates known in the art, for example, salmeterol xinafoate and/or formoterol fumarate. Those skilled in the art will understand that in many cases, salts and/or solvates of a beta-2 agonists will have the desired activity. Accordingly, unless otherwise specified, references to an active ingredient, for example, to salmeterol 1, formoterol 2, isoproterenol 4, albuterol 5, fenoterol, and forskolin, include the compounds themselves as well as a physiologically acceptable analogs, salts, and/or solvates thereof, or combinations thereof.

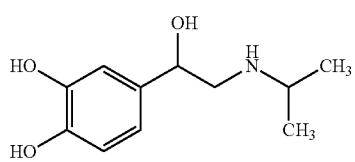

4

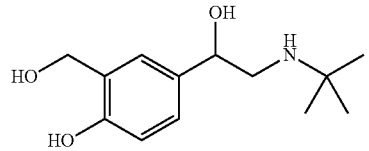

5

Some preferred long-acting beta agonists exhibit high intrinsic adenylate cyclase activity, which increase cAMP synthesis. For example, some embodiments comprise formoterol 2 as a long-acting beta-2 selective agonist, which exhibits some combination of higher potency, reduced systemic effects, high intrinsic activation of adenylate cyclase, and/or increases in cyclic AMP, a mediator of lipolysis.

In some preferred embodiments formoterol 2 is present as a physiologically acceptable salt and/or solvate thereof. Suitable physiologically acceptable salts of formoterol 2 are known in the art, for example, acid addition salts derived from inorganic and organic acids, such as the hydrochloride, hydrobromide, sulfate, phosphate, maleate, fumarate, tartrate, citrate, benzoate, 4-methoxybenzoate, 2-hydroxybenzoate, 4-hydroxybenzoate, 4-chlorobenzoate, p-toluenesulphonate, methanesulphonate, ascorbate, salicylate, acetate succinate, lactate, glutarate, gluconate, tricarballylate, hydroxynaphthalenecarboxylate, oleate, combinations thereof, and the like. Preferred embodiments comprise formoterol 2 as its fumarate salt and/or as a dihydrate. Suitable tissue concentration of formoterol 2 for adipose tissue treatment include from about 1 pM to about 100 μM, more preferably from about 10 pM to about 100 nM.

Some preferred embodiments comprise salmeterol 1 as a long-acting beta-2 agonist. Salmeterol 1 exhibits partial agonist activity, which is believed to reduce receptor desensitization. In some preferred embodiments salmeterol 1 is present as a physiologically acceptable salt and/or solvate thereof. Suitable physiologically acceptable salts of salmeterol 1 are known in the art, for example acid addition salts derived from inorganic and organic acids, such as the hydrochloride, hydrobromide, sulfate, phosphate, maleate, tartrate, citrate, benzoate, 4-methoxybenzoate, 2-hydroxybenzoate, 4-hydroxybenzoate, 4-chlorobenzoate, p-toluenesulphonate, methanesulphonate, ascorbate, salicylate, acetate, fumarate, succinate, lactate, glutarate, gluconate, tricarballylate, hydroxynaphthalenecarboxylate, 1-hydroxy-2-naphthalenecarboxylate, 3-hydroxy-2-naphthalenecarboxylate, oleate, combinations thereof, and the like. Some preferred embodiments comprise salmeterol 1 as the 1-hydroxy-2-naphthalene carboxylate salt (hydroxynaphthoate). Suitable tissue concentration of salmeterol 1 for adipose tissue treatment ranges from about 1 pM to about 100 μM, preferably from about 10 nM to about 10 μM.

Some embodiments comprise optically pure isomers of the beta adrenergic agonist(s), which improve lipolysis and adipogensis inhibition and reduce potential side effects. In some embodiments, these optically pure isomers allow formulations comprising larger loadings of an active ingredient, for example, by eliminating one or more isomers with no physiological effect, a lesser a physiological effect, a negative effect, and/or an undermined physiological effect. Removing the undesired bounds of a racemic mixture isolates the active isomer, or eutomer, thereby allowing more eutomer to be loaded in a give formulation by removing the inactive components.

Two stereogenic centers in a molecule generally generate two diastereomers, referred to herein as (R*,R*) and (R*,S*), and their enantiomers. Diastereomers are stereoisomers that are not enantiomers, that is, the mirror image of one diastereomer is not superimposable on another diastereomer. Enantiomers are stereoisomers that are mirror images of each other. A racemate is a 1:1 mixture of enantiomers. The enantiomers of the (R*,R*) diastereomers are referred to as the (R,R) and (S,S) enantiomers, which are mirror images of each other and therefore share some chemical and physical properties, for example melting points. Similarly, the (R,S) and (S,R) isomers are enantiomers of the (R*,S*) enantiomer. For example, formoterol 2 is available as a racemate of the (R,R)- and (S,S)-isomers in a 1:1 ratio, typically as the dihydrate of the fumarate salt. Some preferred embodiments comprise the (R,R) enantiomer, (R,R)-formoterol, which is more active as a long-acting beta-2 agonist. Some embodiments comprise optically pure isomers of other beta-2 agonists, for example, (R)-salmeterol.

Additionally, in some embodiments of the pharmaceutical composition, at least one long-acting selective beta-2 agonists is highly lipophilic, thereby providing a pharmaceutical composition with sustained activity in fat tissue. It is believed that high lipid solubility extends the residence time of the beta-2 agonist in the adipose tissue, thereby eliminating or reducing the need for a sustained release and/or controlled release carrier in some embodiments. Elimination of a sustained release and/or controlled release carrier provides some combination of simplified formulation, reduced cost, and/or improved safety. In formulations comprising a sustained release carrier, for example, a sustained release polymer, the highly lipophilic of the beta-2 agonist facilitates incorporation into the sustained release carrier, as discussed in greater detail below.

Salmeterol 1 and formoterol 2 have high lipid solubilities, which extends the residence time in the adipose tissue and/or in one or more adipose cells. Some embodiments of the composition comprise a highly lipophilic beta agonist, which reduces or eliminates the need for a sustained or controlled release carrier due to partitioning and sequestration in the adipose tissue thereby prolonging the treatment effect. In some embodiments, beta agonists with an oil-water partition coefficient of at least about 1000 or at least about 10,000 to 1 are preferred. For example, salmeterol 1 is at least 10,000 times more lipophilic than albuterol 5, a short acting hydrophilic beta agonist. Additionally, salmeterol 1 and formoterol 2 have anti-inflammatory properties, used in the treatment of cellulite as discussed below. In some embodiments, they also promote favorable extracellular matrix changes and reduce fluid accumulation, which improves the treatment of cellulite and regional fat accumulation.

Sustained activity is further enhanced by preventing desensitization (tachyphylaxis) that can occur with continuous exposure of adipocytes to adrenergic agonists as discussed above. Compounds that reduce desensitization of the target tissue to the beta-adrenergic receptor agonists are referred to generically as "glucocorticosteroids," although the term encompasses all suitable compounds that reduce tolerance of the target tissue to the beta-adrenergic receptor agonists, including glucocorticosteroids and suitable antihistamines, for example, ketotifen. Glucocorticosteroids are also referred herein as "anti-inflammatory steroids," "glucocorticoids," and/or "corticosteroids." Glucocorticoids are believed to sensitize resistant fat accumulations by increasing the number of beta-2 receptors, thereby favoring lipolysis or fat reduction over fat storage. Glucocorticoids are also believed to decrease the number of alpha-2 receptors. Estrogen can induce the expression of alpha-2 adrenergic receptors in subcutaneous adipose tissue in women resulting in a ratio of beta-2 receptor to alpha-2 receptor of less than 1. A ratio of beta-2 receptors to alpha-2 receptors greater than about 1 is believed to cause fat reduction rather than fat accumulation in adipocytes. Some embodiments of the composition comprising one or more glucocorticosteroids are effective in treating regions of fat comprising a reduced number of beta-2 receptors and or an increased number of alpha-2 receptors, which are resistant to beta adrenergic stimulation of lipolysis or inhibition of adipogenesis, for example, subcutaneous adipose tissue, especially women.

The glucocorticosteroid is believed to improve lipolysis, adipogenesis inhibition, and/or regional fat reduction during beta agonist exposure. In some embodiments, treatment of adipocytes with a glucocorticosteroid that increases lipolytic activity maintains and/or increases both lipolytic activity and the number of beta-receptors in the target tissue. Examples of suitable corticosteroids include dexamethasone 6, prednisolone, fluticasone proprionate 7, budesonide 8, and their analogs. In some preferred embodiments, the glucocorticoid is dexamethasone 6 (9-fluoro-11,17-dihydroxy-17-(2-hydroxyacetyl)-10,13,16-trimethyl-6,7,8,11,12,14,15,16-octahydrocyclopenta[a]phenanthren-3-one, CAS Reg. No. 50-02-2) and/or fluticasone proprionate 7. As discussed above, another preferred compound for reduce desensitization is ketotifen 9, which is also useful as an antihistamine. Some embodiments of the composition comprise one compound that reduces desensitization of the adipose tissue to the beta-2 agonist. Other embodiments comprise a plurality of desensitizing compounds, for example, a plurality of glucocorticosteroids. Some preferred embodiments comprise at least one glucocorticosteroids and the antihistamine ketotifen. It is believed that the combination of glucocorticosteroid and ketotifen is more effective at reducing desensitization because ketotifen prevents beta receptor sequestration, while the glucocorticosteroid increases the beta-receptor number, thereby synergistically potentiating the overall effect on the beta receptor. Analogs of ketotifen are also suitable.

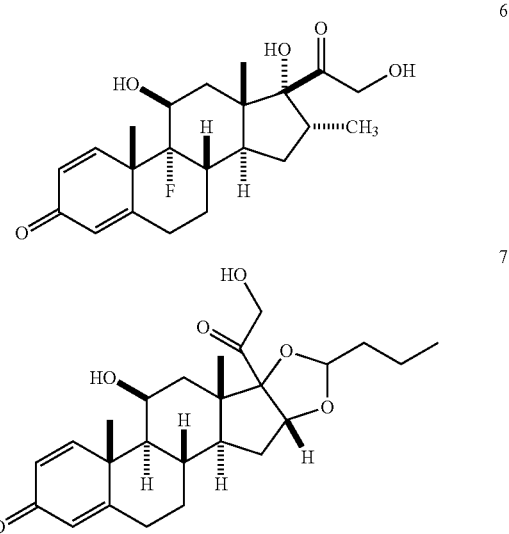

8

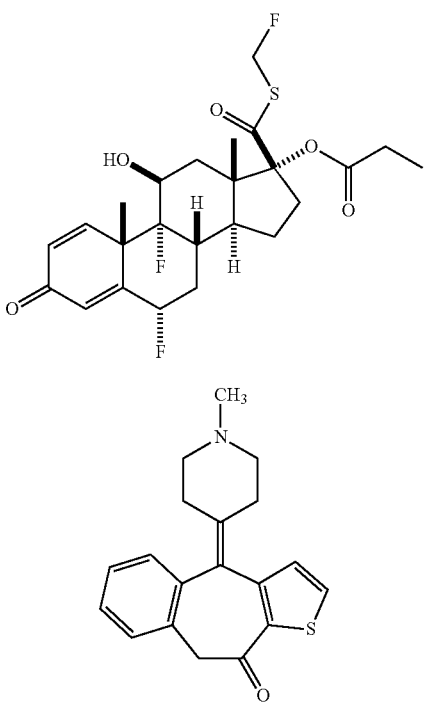

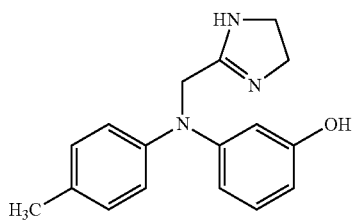
10

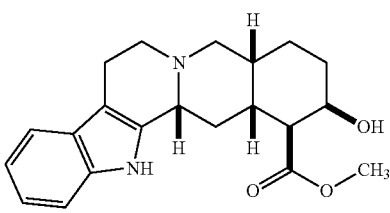
11

9

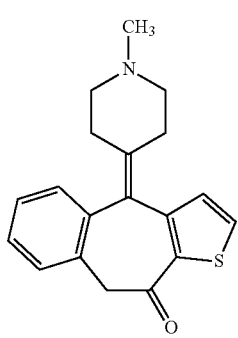

Some embodiments of the composition comprise other adrenergic agents that enhance the effect of the long-acting selective beta-2 agonist. For example, aminophylline 12 (1,3-dimethyl-7H-purine-2,6-dione, diethylamine CAS Reg. No. 317-34-0) and theophylline 13 (CAS Reg. No. 58-55-9) are lipolytic agent that block the breakdown of cyclic AMP.

In some embodiments, at least one of beta-2 receptor activity or density increases in human subcutaneous adipocytes in response to the anti-inflammatory steroid or ketotifen administration, particularly in the presence of a beta agonist. In some embodiments, increasing beta-2 receptor activity and/or density potentiates the effect of long- and short-acting beta-2 agonists. Additionally, in some embodiments, it is believed that glucocorticosteroid exposure downregulates anti-lipolytic alpha-2 adrenergic receptors, which is particularly beneficial, for example, in subcutaneous fat, which often has a high number of these receptors. Thus, in some embodiments, the glucocorticosteroid sensitizes subcutaneous fat to the effects of beta-2 receptor stimulation, lipolysis, inhibition of adipogenesis, and/or apoptosis, and/or increases the ratio of beta-2 adrenergic receptors to alpha-2 adrenergic receptors, thereby shifting the balance of the adipose tissue from fat accumulation to fat loss.

Some embodiments of the composition comprise additional optional ingredients. For example, certain fat accumulations such as cellulite and lipomas comprise fibrous connective tissue. In some situations, it is advantageous to degrade this fibrous connective tissue, for example, to improve the appearance of the overlying skin. Some embodiments of the composition comprise an enzyme such as collagenase, which degrades the collagen in the fibrous connective tissue.

Some embodiments of the composition comprise one or more anti-lipolytic blocking agents known in the art, for example, selective alpha-2 receptor antagonists such as phentolamine 10 (CAS Reg. No. 73-05-2) or yohimbine 11 (CAS Reg. No. 146-48-5) block anti-lipolytic effects in regional fat accumulation. Anti-lipolytic effects in adipocytes and adipose tissue are typically observed in subcutaneous and regional areas of fat accumulation. For example, when exposed to beta agonists, subcutaneous fat has a lower lipolytic rate than visceral fat. Exposing subcutaneous fat to anti-lipolytic blocking agents improves lipolytic activity in some embodiments.

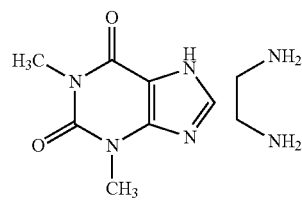
12

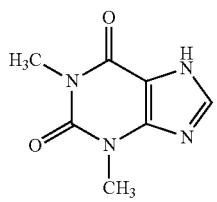
13

Other optional ingredients increase the secondary signals created by the beta agonist binding. For example, in some embodiments, some embodiments, the composition comprises forskolin 14 (CAS Reg. No. 66575-29-9), which stimulates adelylate cyclase, thereby increasing the synthesis of cyclic AMP initiated by the long-acting beta agonist. The increased concentration of cyclic AMP helps sustain lipolytic activity.

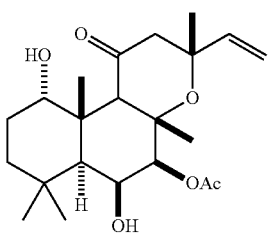
14

Some embodiments of the composition comprise growth hormone in combination with a long-acting beta agonist and glucocorticosteroid, which appears to stimulate lipolysis.

Others embodiments of the composition further comprises one or more nonselective beta agonists, for example, isoproterenol 4, and/or short-acting selective beta-2 agonists, for example, terbutaline. Some compositions comprise at least one of an alpha-2 antagonist, or physiologically acceptable salts or solvates thereof.

Embodiments of the composition are formulated for administered by any suitable method known in the art, for example, as described in *Remington: The Science And Practice Of Pharmacy* (21st ed., Lippincott Williams & Wilkins). In some embodiments, the composition is formulated for injection of an area at which treatment is desired, for example, at a subcutaneous fat deposit.

Suitable excipients for injectable formulations are known in the art. In some embodiments, one or more of the beta-2 receptor agonists or glucocorticosteroids are formulated in a liquid carrier, for example, as a solution, a suspension, a gel, and/or an emulsion. Some embodiments comprise any suitable lipophilic excipient known in the art, for example, modified oils (e.g., Cremophor® BASF), soybean oil, propylene glycol, polyethylene glycol, derivatized polyethers, combinations thereof, and the like. Some embodiments comprise a microparticulate and/or nanoparticulate carrier for at least one of the beta-2 receptor agonists and/or glucocorticosteroids, as discussed in greater detail below. Some embodiments comprise one or more sustained or controlled release carriers or agents, for example, polymer microspheres.

Injectable formulations are administered using any mean known in the art, for example, using a single needle, multiple needles, and/or using a needleless injection device. In some embodiments, a tissue loading dose of the active ingredients formulated in a suitable carrier delivered by injection. In some embodiments, delivery comprises single needle injection. In some embodiments, delivery comprises injection using a multi-needle array, which, in some embodiments, provides a wide dispersion of the formulation in the target tissue. In some embodiments, formulations are injected in a manner that allows dispersal into the appropriate layer of subcutaneous fat in areas where regional fat reduction is desired, such as the submental region, the waist/hip, the lateral buttocks or thigh, or the periorbital fat regions. In some embodiments, the formulation is injected in aliquots of from about 0.5 mL to about 1.0 mL. In some embodiments, aliquots of the formulation are injected over an area of from about 10 cm$^2$ to about 20 cm$^2$.

Another delivery mode comprises a needleless pressurized injection device. In some embodiments, of these devices, the formulation is pressurized mechanically or pneumatically, for example, using a gas such as helium or carbon dioxide, and then forced through a small orifice into the body tissues, thereby delivering the formulation subcutaneously. Suitable formulations for needleless injection are known in the art, for example, liquid, solutions, suspensions, gels, colloids, emulsions, and dry powders. An advantage of this system is a wide dispersal area compared with typical needle injection systems. Needleless injection under the appropriate pressure forces the formulation into a more planar delivery pattern, with fingers of formulation spreading out radially following paths of least resistance. In contrast, delivery by a typical needle injection results in a globular delivery of the formulation. Needleless injection also permits precise control of the depth of penetration by controlling the injection pressure and orifice size. Thus, needleless injection is a preferred delivery method for a sub-dermal injection of a formulation for treating superficial fat accumulations, which is useful, for example, for smoothing skin dimpling caused by fat. In some embodiments, needleless injection is also used for deeper, sub-dermal sub-fascial injections targeting deeper fat accumulations. A needleless device also provides easy and convenient multiple injections of the formulation over a defined region with a large lateral spread.

In some embodiments, the beta-2 agonist and compound that reduces desensitization are administered separately, for example, injected as separate formulations. Co-administration of a beta-2 agonist with a compound that reduces desensitization is preferred in some embodiments, however, because the reduced desensitization is observed only in the presence of the beta-2 in some cases.

Some embodiments of the formulation comprise one or more sustained or controlled release agents known in the art for providing a sustained or controlled release of a beta-2 agonist and/or glucocorticosteroid, which are, for example, encapsulated in, bound to, and/or conjugated to the sustained or controlled release agent or carrier. In some embodiments, biocompatible, biodegradable sustained or controlled release formulations provide local tissue activity for weeks to months. Suitable sustained or controlled release agents or carriers are known in the art, for example, polymers, macromolecules, active ingredient conjugates, hydrogels, contaminations thereof, and the like. Some embodiments of the sustained release carrier target fat, for example, liposomes. Preferably, the sustained release materials are selected to facilitate delivery of a substantially equal amount of the active substance per unit time, particularly over the course of at least about 3 days, more particularly at least about 4 days, to up to one year or greater. Several rounds of injections of the sustained release formulation can be made over time to treat a single area.

In some embodiments, the sustained release agent comprises a polymer, for example, polylactides, polyglycolides, poly(lactide glycolides) polylactic acids, polyglycolic acids, polyanhydrides, polyorthoesters, polyetheresters, polycaprolactones, polyesteramides, polycarbonates, polycyanoacrylates, polyurethanes, polyacrylates, and blends, mixtures, or copolymers of the above, which are used to encapsulate, binds, or conjugate with the active ingredients(s) (e.g., beta agonists and/or glucocorticosteroids). Some preferred embodiments of sustained release polymers comprise polyethylene glycol groups to which one or more of the active ingredients is conjugated. In some preferred embodiments, the sustained release agent comprises poly(lactide glycolide) (PLGA, polylactic-co-glycolic acid)) copolymer 15.

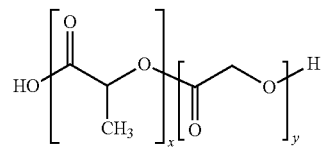

15

Some embodiments of the sustained release agent comprise one or more hydrogels known in the art, for example, modified alginates. Examples of suitable modified alginates include those disclosed in WO 98/12228. Some embodiments of the sustained release agent comprise an albumin-based nano-particle carrier or excipient.

In some embodiments, a formulation comprising a pre-polymer solution is injected into the target tissue site, where it is then polymerized (e.g., by photopolymerization) or solidified (e.g., by using temperature sensitive gelling materials) in vivo.

In some embodiments, the controlled release materials here release characteristics designed for the particular application of tissue reduction. In some embodiments, the sustained release or controlled release agent is formed into microparticles, such as microspheres, which are formulated as an injectable solution and/or gel. In some embodiments, the microparticles are from about 10 µm to about 100 µm in diameter and generally uniform in size. For example, in some embodiments, formulations comprising alginates and/or poly(lactide-co-glycolide)s 15 are provided as an injectable gel or processed into microspheres using methods known in the art. Other examples of suitable injectable biodegradable, biocompatible materials suitable for microparticle formation include chitosan, dextran, hydroxyapetite, and silicon.

Microspheres and/or microparticles are formed using any method known in the art, for example, by a solvent evaporation and/or emulsion polymerization. In some embodiments, the microspheres have average diameters of from about 5 µm to about 60 µm, preferably, about 20 µm. In some embodiments, PLGA is manufactured with varying ratios of lactide to glycolide depending on the desired rate of release of the active ingredient(s). Because the rate of degradation of this copolymer is proportional to its crystallinity and the proportion of glycolide in the formulation, non-racemic mixtures of the lactide and/or glycolide increase crystallinity and slow the rate of degradation. Higher proportions of glycolide increase the rate of degradation. In some embodiments, a ratio of about 65%-75% lactide to about 25%-35% glycolide provides active ingredients released over from about 2 weeks to about 45 days. In other embodiments, the ratio of lactide to glycolide is from about 0:100 to about 100:0, thereby providing other release rates.

Some embodiments of the microspheres or microparticles comprise hollow and/or porous interiors. In some embodiments, the microspheres comprise a solid or porous outer shell. Some embodiments of formulations comprising a porous outer shell and/or micro sphere exhibits a biphasic release profile of the active ingredient(s) with an initial release burst of the active ingredient(s), followed by a sustained release associated with degradation of the polymeric microspheres. The initial burst loads the tissue with an effective lipolytic/adipogenesis inhibitory concentration of the active ingredient(s), with the subsequent slower release maintaining the desired concentration. In some embodiments, the different microsphere structures and active ingredient release profiles optimize the treatment effect of adipose tissue and adipocytes through adrenergic receptor modulation. In some preferred embodiments, sustained local tissue concentrations of long-acting selective beta-2 adrenergic agents, such as salmeterol 1 and/or formoterol 2 at concentrations of about 10 µM to about 10 µM.

In some embodiments, one or more of the active ingredients are encapsulated, bound, and/or conjugated to the polymer at a ratio of about 10-12% by mass compared to the polymer microspheres. The amount of active ingredient as a mass percentage of the carrier (e.g., microparticles or microspheres) is referred to herein as "active ingredient loading." As used herein, the terms "loaded" and "loading" refer to active ingredients substantially encapsulated bound, and/or conjugated to a carrier. In some embodiments, the active ingredient loading is up to about 75%. Thus, some preferred formulations comprise one or more beta-2 adrenergically active ingredients, such as salmeterol 1, formoterol 2, and/or their physiologically acceptable salts and solvates, loaded on polymer microspheres at about 1 mg to about 20 mg of active ingredient per about 10 to about 200 milligrams of polymer. In some embodiments, a formulation with this active ingredient loading is sufficient for providing from about 15 days to about 45 days of active ingredient release at a concentration suitable to produce lipolysis and/or adipogenesis inhibition.

In some embodiments, two or more active ingredients are loaded into the same microsphere, for example, in a liposome. Thus, some embodiments, a polymer encapsulating a glucocorticosteroid in the adrenergic compound is delivered simultaneously to the adipose tissue. Alternatively, the two active ingredients are loaded on separate microspheres. The two types of microspheres are then mixed to obtain a formulation with the desired ratio of beta-receptor agonist and glucocorticosteroid, then administered simultaneously. Alternatively, the two types of microspheres are administered sequentially.

The microspheres comprising the active ingredient(s) are suspended in from about 10 mL to 20 mL of an appropriate physiologically acceptable liquid carrier. In some embodiments using separate microspheres of the active ingredients, the microspheres are mixed together in the liquid carrier. In other embodiments, each type of microspheres is separately mixed with a liquid carrier. In some embodiments, the microsphere suspension is then injected subcutaneously just below the dermis in 1.0 mL aliquots to cover an approximate 2.0 $cm^2$ area per mL of the microsphere suspension, for example, for the treatment of cellulite. In some embodiments, from about 10 to about 20 injections are administered to cover an area of from about 20 $cm^2$ to about 40 $cm^2$. Larger and/or smaller areas are treated in other embodiments. Alternatively, bolus injections 1.0 mL to 10.0 mL are injected into fat accumulations, such as the periorbital regions, submental regions, lateral hips, and buttocks. Alternatively, injections as described above are made separately and sequentially in the same locations using two microsphere formulations encapsulating each active ingredient.

In some embodiments using needleless injection, the microparticulate formulations are injected as suspensions or as the powdered loaded microparticles, that is, without a liquid carrier.

In some embodiments, the glucocorticosteroid, such as dexamethasone 6, budesonide 8, and/or fluticasone propionate 7, also act as anti-inflammatory agents thereby reducing inflammation caused by administration of the formulation, for example, caused by polymers, polymeric microspheres, and/or liposomes in a sustained release formulation.

PLGA 15 microspheres encapsulate hydrophobic compounds more readily than hydrophilic compounds. To increase loading of hydrophilic active ingredients, in some embodiments, the microspheres are modified with polyethylene glycol units, as discussed above. Microspheres of certain sizes are substantially not absorbed into the blood or removal by lymph, thereby providing release of the active ingredient(s) in the desired location. For example, in some embodiments, the microspheres are from about 20 µm to about 200 µm in diameter. In some embodiments, the size of the microsphere also affects the release profile of the active ingredient(s) in the tissue. In general, larger microspheres tend to provide a longer and more uniform release profile.

An exemplary sustained release formulation comprises about 0.5 milligrams to about 7.5 milligrams of salmeterol 1 and/or formoterol 2, and about 1.5 milligrams to about 7.5 milligrams of dexamethasone 6, fluticasone propionate 7, and/or budesonide 8 encapsulated in about 100 milligrams of polylactide glycolide (PLGA) 15 copolymer microspheres at a ratio of about 70 lactide:30 glycolide. In some embodiments, the copolymer ratio and active ingredient encapsulation deliver up to about 1.0 µg per day of salmeterol 1 and/or up to about 0.5 µg of formoterol, and up to 5 µg per day of fluticasone and/or budesonide 6 per about 1 mg of copolymer for up to about 30 days.

Some embodiments comprise non-sustained release formulations. In some embodiments, the duration of activity of long-acting selective beta-2 agonists in non-sustained release formulations, after a signal dose, is greater than about four hours and preferably up to about 12, or up to about 24 hours. In contrast, short-acting selective beta-2 agonists under similar conditions, have activities of less than about four hours and is less than about one hour. An exemplary non-sustained release injectable formulation comprises from about 100 µg to about 250 µg of salmeterol xinafoate and from about 500 µg to about 1000 µg of fluticasone propionate 7 formulated in up to about a 10 mL lipid-based excipient such as Cremophor® or equivalent.

In some embodiments, formulations are delivered transdermally using any suitable method known in the art, for example, as a topically applied cream or through a patch. Alternatively, other transdermal delivery means known in the art are also useful, for example, electrical. In particular, long-acting beta-2 agonists, such as formoterol 2, salmeterol 1, or bambuterol 3, and glucocorticosteroids are suited for topical application to the skin due to their hydrophobicity. Sustained release embodiments of transdermally deliverable formulations are provided as known in the art, for example, using a biodegradable, biocompatible active ingredient-polymer formulation or liposome formulation, as discussed above.

While certain embodiments have been described, these embodiments have been presented by way of example only, and are not intended to limit the scope of the disclosure. Those skilled in the art will understand that the formulations, methods, and systems described herein may be embodied in a variety of other forms. Furthermore, various omissions, substitutions and changes in the form of the formulations, methods, and systems described herein may be made without departing from the spirit of this disclosure. The accompanying claims and their equivalents are intended to cover such forms or modifications.

What is claimed is:

1. An injectable formulation for treating regional fat deposits comprising:
    (a) a therapeutically or cosmetically effective amount of a lipophilic, long-acting, selective beta-2 adrenergic receptor agonist that comprises salmeterol, bambuterol, or formoterol, physiologically acceptable salts or solvates thereof, or combinations thereof in an amount that is up to about 250 micrograms, and
    (b) a physiologically acceptable excipient;
    provided that the formulation is formulated for injection into a layer of subcutaneous tissue to a human.

2. A method for treating regional fat deposits comprising the step of providing by subcutaneous injection the formulation of claim 1 to a human.

3. The method of claim 2, wherein the beta-2 adrenergic receptor agonist comprises at least one of salmeterol or formoterol, or a salt or solvate thereof, or a combination thereof.

4. The method of claim 2, wherein the beta-2 adrenergic agonist is salmeterol, or its salt, solvate, or a combination thereof.

5. The method of claim 4, wherein the beta-2 adrenergic agonist is salmeterol xinafoate.

6. The method of claim 4, wherein the effective amount of salmeterol or its salt, solvate, or combination thereof is up to about 100 micrograms.

7. The method of claim 2, wherein the beta-2 agonist is formoterol, or its salt, solvate, or combination thereof.

8. The method of claim 7, wherein the beta-2 agonist is formoterol fumarate.

9. The method of claim 7, wherein the effective amount of formoterol or its salt, solvate, or combination thereof is up to about 50 micrograms.

10. The method of claim 2, wherein the formulation is delivered by injection using a syringe.

11. The method of claim 2, wherein the formulation is delivered by needleless injection.

12. The method of claim 2, wherein the providing step comprises contacting the formulation with the fat accumulation, adiposity, adipose tissue, or cellulite of the human.

13. The method of claim 12, wherein the fat accumulation, the adiposity, the adipose tissue, or the cellulite is located in the waist or abdominal region of the human.

14. The method of claim 12, wherein the fat accumulation, the regional adiposity, or the adipose tissue is subcutaneous fat.

15. The method of claim 12 that results in a region of adipose tissue of the human exhibiting sustained adrenergic activity.

16. The method of claim 2, wherein the method provides an effect that is at least partially cosmetic.

17. The method of claim 2, wherein the method provides an effect that is at least partially therapeutic.

18. The method of claim 15 provided that the sustained adrenergic activity is exhibited after about 15 days of the contacting step.

* * * * *